(12) United States Patent
Rohler et al.

(10) Patent No.: US 8,891,849 B2
(45) Date of Patent: Nov. 18, 2014

(54) EXTENDED LOW CONTRAST DETECTABILITY FOR RADIOGRAPHIC IMAGING SYSTEMS

(75) Inventors: David P. Rohler, Shaker Heights, OH (US); Arjun K. Maniyedath, Twinsburg, OH (US); Thomas L. Toth, Brookfield, WI (US); Thomas E. Dechant, Chagrin Falls, OH (US); Steven H. Izen, Shaker Heights, OH (US)

(73) Assignee: Tip Imaging, LLC, Shaker Heights, OH (US)

( * ) Notice: Subject to any disclaimer, the term of this patent is extended or adjusted under 35 U.S.C. 154(b) by 97 days.

(21) Appl. No.: 13/503,721

(22) PCT Filed: Jul. 16, 2010

(86) PCT No.: PCT/US2010/002006
§ 371 (c)(1),
(2), (4) Date: Apr. 24, 2012

(87) PCT Pub. No.: WO2011/008296
PCT Pub. Date: Jan. 20, 2011

(65) Prior Publication Data
US 2012/0230576 A1   Sep. 13, 2012

Related U.S. Application Data

(60) Provisional application No. 61/271,150, filed on Jul. 17, 2009, provisional application No. 61/278,954, filed on Oct. 14, 2009.

(51) Int. Cl.
*G06K 9/00* (2006.01)
*A61B 6/00* (2006.01)
*A61B 6/03* (2006.01)

(52) U.S. Cl.
CPC ............. *A61B 6/482* (2013.01); *A61B 6/032* (2013.01); *A61B 6/583* (2013.01); *A61B 6/545* (2013.01); *A61B 6/405* (2013.01)
USPC ....................................................... 382/132

(58) Field of Classification Search
None
See application file for complete search history.

(56) References Cited

U.S. PATENT DOCUMENTS

| | | | |
|---|---|---|---|
| 7,356,174 B2 * | 4/2008 | Leue et al. | 382/131 |
| 7,813,471 B2 | 10/2010 | Hirokawa et al. | |
| 2006/0109953 A1 * | 5/2006 | Walter et al. | 378/5 |
| 2009/0141854 A1 | 6/2009 | Hirokawa et al. | |
| 2011/0200167 A1 * | 8/2011 | Naidu et al. | 378/19 |

* cited by examiner

*Primary Examiner* — Atiba O Fitzpatrick
(74) *Attorney, Agent, or Firm* — Tucker Ellis LLP

(57) ABSTRACT

Systems and methods for determining an extended low contrast detectability performance function for an operating range for a core operating mode of a radiographic imaging system using actual reconstructed images characterize the contrast performance of a radiographic imaging system over its operating range and for any patient size based on the off-line calibration, uses ordered pairs of flux index and contrast index for each scanned object to provide a contrast index for each protocol for each contrast set, and uses the ordered pairs of flux index and contrast index to determine an extended low contrast detectability performance function for the operating range of a radiographic imaging system. Extended low contrast detectability performance data compilation and methods of clinical use, and low contrast phantom configurations and methods of calibration are also disclosed.

20 Claims, 30 Drawing Sheets

GRAY: ORIGINAL PIN, BLUE: RECONSTRUCTED PIN, RED: INTREGAL INSIDE PIN REGION

PIN SIZES: 2.0, 2.5, 3.3, 4.3, 5.5, 7.0, 9.0, 11.7, 15.0

EXTENDED LOW CONTRAST DETECTABILITY FOR RADIOGRAPHIC IMAGING SYSTEMS

RELATED APPLICATIONS

This application claims priority to U.S. Provisional Patent Application No. 61/271,150 filed Jul. 17, 2009 and U.S. Provisional Patent Application No. 61/278,954, filed Oct. 14, 2009, both of which are incorporated herein by reference.

FIELD OF THE INVENTION

The present invention is in the general field of radiology and imaging, and more particularly in the field of radiographic imaging.

BACKGROUND OF THE INVENTION

Because radiographic imaging, including computed tomography (CT) has the capability of detecting small low contrast features, it has become an integral part of radiology medical practice, allowing medical practitioners to detect low contrast tumors and lesions in soft tissue anatomical regions including the brain and the liver. Low contrast detection is an important characteristic of diagnostic x-ray imaging methods. An important issue in radiology today is how to reduce the radiation dose during CT examinations without compromising the image quality. Generally, higher radiation doses result in the ability to detect lower contrast smaller objects, while lower doses lead to increased image noise. Increased radiation dosage increases the risk of radiation induced cancer.

The descriptions in this patent are focused on computed tomography (CT) but the application of the technology described is not limited to CT. The technology described can be applied to other radiographic imaging systems as well so that references in this patent to "CT" or "CT scanner" should be interpreted as applying to other radiographic imaging systems.

The ability of a CT system to differentiate a low-contrast object from its background is measured by its low contrast detectability (LCD). LCD is measured with phantoms that contain low-contrast objects of various sizes. Phantoms that produce low contrast objects by using materials with different densities are useful for testing conventional energy integrating CT scanners. Phantoms that produce low contrast objects using energy sensitive materials would allow performance testing for a dual energy scanner.

The low-contrast resolution of a CT scanner is generally defined as the smallest object that can be detected at a given contrast level and dose. The contrast level is usually specified as a percentage of the linear attenuation coefficient of water. A sample specification with the current method might be "4 mm at 0.3% contrast for 10 mm slice thickness at 30 mGy CTDIvol dose." Sometimes other dose metrics are used such as the surface dose measured at the outer surface of the phantom.

The current LCD specification is made at a single protocol in one of two ways:
1. human observation—reconstructed images are viewed by one or more human observers to determine the smallest pin that is visible in the opinion of the observer;
2. statistical method—an automated algorithm predicts from a flat "water" image the contrast required to detect a given size pin with a specified confidence interval.

In this description, it will be shown that the current LCD specification is inadequate in that it characterizes the performance of the CT scanner at only one protocol and that it is necessary to characterize the performance over an extended range including, for example, the full operating range of the scanner.

Contrast Index

In order to extend the measurement of low contrast detectability, a new contrast measure, M can be used, as defined in one way for example by Equation 1, $$M = \frac{M_0}{cp}, \quad (1)$$

and designated as "contrast index." In Equation 1, p is the smallest pin size, measured in millimeters, visible at contrast level, c, measured in Hounsfield units (HU) where one Hounsfield unit corresponds to 0.1% of water attenuation and $M_0$ is an arbitrary constant for bringing the measure, M, into a convenient numerical range. It is important to note that the contrast level, c, in this definition is the nominal or expected contrast level of the object as opposed to a measured contrast level, later indicated with an upper case C. In this example, $M_0=6000$ in order to map the best current contrast specification of 2 mm at 0.3% to a contrast measure of 1000. For example, the specification, "4 mm at 0.3% contrast for 10 mm slice thickness at 30 mGyCTDIvol," would generate a contrast measure of 500, $$M = \frac{6000}{(3)(4)} = 500. \quad (2)$$

Flux Index

Commercial CT scanners typically operate over a wide range of protocols, each of which can have distinct contrast characteristics. The protocol parameters that impact contrast include (1) scan time, (2) tube current (mA), (3) slice thickness, (4) object diameter, (5) tube voltage (kVp) and (6) x-ray filter. Also, contrast is significantly impacted by non-linear reconstruction methods as well as the reconstruction pixel size and reconstruction filter. It is assumed in the following that the tube voltage, the x-ray filter, the scan diameter and the reconstruction method, collectively comprising a core operating mode, are fixed and that the scanner, in that core operating mode, can be characterized by the CTDIvol dose index. Then the parameters that directly affect the x-ray flux available for detection are:
 1. scan time (0.25-2.0 sec/revolution)
 2. x-ray tube current (20-400 mA)
 3. slice thickness (0.5-10.0 mm)
 4. object diameter (20-50 cm)
 5. dose index (CTDIvol)
A relative flux measure, designated as the "flux index," incorporates these 5 parameters as follows.

$$FluxIndex = \quad (3)$$
$$\frac{CTDIvol}{CTDIvol_{ref}} * mA * sliceThick * scanTime * \frac{e^{-objDiam*attWater}}{e^{-refDiam*attWater}}$$

$refDiam = 20.0$ cm

CTDIvol is per 100 mAs and CTDIvol$_{ref}$ is an arbitrary constant dose reference value per 100 mAs that will be determined for each core operating mode tested. For practical combinations of these parameters, the range of Flux Index is approximately [0.1, 7,000.0]. An example of a current LCD specification could be "4 mm at 0.3% for 10 mm slice at 90 mAs." Since this example relates to the 20 cm CATphan, the Flux Index would be 900.

The relative flux index, described above, relates linearly to dose except for the factor involving the object diameter. The currently accepted dose index for CT is CTDIvol as defined in IEC 60601-2-44. Dose is linearly related to flux for a given object size and slice thickness. The contrast measurements discussed in this paper are generally accomplished at the center of the object. For that reason, the derivation and the description of the ExLCD method is currently based on the relative flux index.

ExLCD Graph

As described above, the range of flux index for a CT scanner is approximately [0.1, 7,000.0]. It can be demonstrated that the corresponding range of contrast index is approximately [0.5, 1000.0]. These ranges define the scope of the ExLCD graph, shown in FIG. 27 in log-log format.

Larger values of Contrast Index indicate better image quality or the ability to detect smaller, lower contrast objects. Smaller values of Contrast Index indicate poorer image quality or the ability to detect only larger, higher contrast objects.

Larger values of Flux Index indicate higher dose or smaller patient sizes. Smaller values of Flux Index indicate lower dose or larger patient sizes.

The current LCD methods often utilize the CTP515 low contrast module (FIG. 5) of the CATphan phantom (FIG. 4). [The Phantom Laboratory, http://www.phantomlab.com/pdf/catphan600_download.pdf] The "supra-slice" contrast sets are used but only the lowest 0.3% contrast set is typically reported.

There are two LCD measurement methods currently used on commercial CT scanners: (1) human observer method and (2) statistical method. We have compiled some recent reported measurements from the major CT manufacturers and collected them in Table 1. [NHS Purchasing and Supply Agency, Buyer's Guide, Computed Tomography Scanners, Reports CEP08007, CEP08027, CEP08028].

above, it is not clear whether a single observer or multiple observers were used. It is also not clear how the specific protocol was selected to derive the reported specification. At the present time, it is believed that all of the CT manufacturers except one use the observer method.

Statistical Method

At the present time, it is believed that the statistical method is used only by one CT manufacturer. The statistical method for LCD avoids the problems associated with human observers. The method relies only on noise measurements in a reconstruction. It does not use a phantom with actual contrast objects. It analyzes image noise in a specific manner that determines the amount of contrast needed to detect an object of a given diameter relative to the background with a stated level of confidence. Because the assessment is made by the computer and not a human observer, the method is highly repeatable and reproducible. However the statistical method cannot differentiate contrast performance resulting from non-linear reconstruction methods since only a noise image is evaluated. The performance of the system relative to how well the original low contrast object is preserved cannot be determined. As discussed in more detail later, this is true of any noise analysis method that does not measure an actual object.

Quantum Noise Limited

An imaging system is said to be "quantum noise limited" if, for all practical purposes, the only source of image noise is the statistics of finite x-ray quanta. In the context of Equation 13, a quantum noise limited system is one in which the electronic noise is absent, i.e., when. The plots in FIG. 3 illustrate the S/N as a function of relative x-ray Flux Index. In a log-log plot, the S/N ratio for a quantum noise limited system (green trace) will be represented by a straight line whose slope is ½. If electronic noise (system noise) is present the overall S/N will be significantly impacted only for lower flux values as shown by the red trace in FIG. 3.

It is reasonable to predict that a contrast measure over the full range of scanner protocols and body sizes will have a form similar to the S/N as shown in FIG. 3. For example, a scanner may exhibit contrast measurements such as those shown in the upper plot in FIG. 7. Then it would be possible to accurately characterize the contrast performance of the CT scanner with a curve such as the red one shown in the lower plot in FIG. 7.

TABLE 1

Recent reported LCD measurements from major CT manufacturers.

| Contrast Index | Scanner | Contrast | Pin Size | Dose | Slice Thickness | mAs | Color Code | Flux Index |
|---|---|---|---|---|---|---|---|---|
| 500 | A | 0.3% | 4 mm | 10 mGy | 10 mm | 90 | red | 900 |
| 400 | B | 0.3% | 5 mm | 16 mGy | 10 mm | 180 | blue | 1,440 |
| 1,000 | C | 0.3% | 2 mm | 40 mGy | 10 mm | 350 | green | 3,600 |
| 400 | D | 0.3% | 6 mm | 7.8 mGy | 10 mm | 105 | yellow | 657 | source: NHS Purchasing and Supply Agency, Buyer's Guide, CT Scanners

It is instructive to convert these reported measurements to Contrast Index and Flux Index values and show them on an ExLCD graph (FIG. 6) based on the above definitions of ExLCD Contrast Index and Flux Index.

Human Observer Method

Currently, LCD is determined by scanning the CATphan under selected protocol techniques and reconstructing the image(s). One or more human observers are then presented with the images to render an opinion regarding the smallest object they believe is visible and therefore detectable for the 0.3% contrast set. For the reported measurements described With the current LCD method, however, a scanner is characterized with only ONE contrast measurement taken at a single protocol, illustrated by the bold red + and the dotted vertical line in the upper plot in FIG. 8. This single measurement does not characterize the contrast performance of the scanner. In fact, it significantly misconstrues the true contrast performance of the scanner. As shown in the lower plot in FIG. 8, the single protocol measurement implies contrast performance that follows a quantum noise limited curve defined by the single measurement as shown by the dashed line in the lower plot in FIG. 8. The inaccuracy of the single protocol contrast performance curve is illustrated in FIG. 9. Additionally, the current LCD methods do not adequately handle smaller pins, those that are impacted by system blurring, i.e. the Modulation Transfer Function (MTF). The profiles in FIG. 10 illustrate the problem with smaller pins. In FIG. 10 only pin sizes, 15, 7, 5, 3 and 2 mm are shown.

Conventional detectability methods that are based only on a noise analysis such as the statistical method, noise power spectrum, simple-pixel standard deviation or matched filter standard deviation all can over estimate the performance of a reconstruction process that alters the contrast of the test object. Given reconstruction processes that limit spatial bandwidth of both noise and object, conventional detectability methods will not account for changes in the assumed object. For example assume that a small pin in an LCD test phantom is exactly a cylinder with a 2 mm diameter and a contrast of 0.3%. If perfectly reconstructed, image pixels within the area of the pin will have an average contrast of 0.3% and all pixels outside this region will be 0%. However the MTF of the system will blur the pin especially at its edges and spread some of its contrast into pixels beyond the original geometric boundary. This results in a reduction in average contrast within the pin region.

From the narrative above, we obtain an intuitive sense about the inaccuracies of the single protocol LCD method. These inaccuracies occur for one or more of the following reasons that will be described in more detail later in this document.

1. human observer variation
2. finite pin size selections
3. selection of protocol
4. presence of system (electronic) noise
5. impact of system blurring (MTF) on smaller pins The low contrast detectability (LCD) performance of a CT system is a critical performance characteristic, providing a measure of the scanner's ability to produce high quality images at the lowest possible x-ray dose. Because it is increasingly important to utilize lower dose protocols in present day CT scanners, it is now critical that LCD be measurable over the entire range of protocols and body sizes.

In the lower graph in FIG. 7 we illustrate an ExLCD contrast performance curve for a typical (simulated) CT scanner. CT systems vary in their contrast performance based on the following system characteristics:

1. overall dose/quantum efficiency
2. system/electronic noise
3. system blurring (MTF)
4. non-linear reconstruction methods The dotted and dashed traces in the upper plot in FIG. 11 illustrate qualitatively how the contrast performance curve is impacted by some of these system characteristics. The lower plot illustrates the significance of those performance curve variations relative to dose. In that plot, the red line intersections show the relative dose required to achieve similar image quality on each of the respective scanners.

The three colored or shaded traces in the upper plot in FIG. 12 illustrate how three representative CT scanners might be compared. In the lower plot, the representative CT scanner performance curves are overlaid on the error region of the single protocol contrast method, illustrating that the inaccuracies of the current LCD method may effectively prohibit true differentiation of the contrast performance between CT scanners.

SUMMARY OF THE INVENTION

The present disclosure and related inventions are of an Extended Low Contrast Detectability (also referred to herein as "ExLCD" or "Extended LCD") contrast measurement system and method that provides a robust capability to connect x-ray dose with a universal image quality metric. The disclosure and related inventions provide the capability to:

1. characterize the contrast performance of any radiographic imaging system over its operating range and for any patient size, based on the off-line calibration, providing the capability for QA performance testing including the capability to track the contrast performance of a radiographic imaging system over time,
2. compare the contrast performance of two or more radiographic imaging systems, including, for example for CT scanners, contrast performance impacted by non-linear or iterative reconstruction,
3. standardize protocols across different radiographic imaging systems by identifying protocols on each system that relate to equivalent contrast index levels,
4. optimize the scanning protocol on a specific radiographic imaging system for a specific patient in a clinical scenario for a desired contrast index level, thereby enabling a radiographic imaging system's ability to perform lower dose scans with good image quality.

Each of these features can occur if contrast performance curve(s) have been obtained according to the Extended Low Contrast Detectability (ExLCD) technology of the present disclosure.

In accordance with one aspect of the disclosure and related inventions, there is provided a method of determining an extended low contrast detectability performance function as a relation between a flux index and a contrast index for an operating range for a core operating mode of a radiographic imaging system using actual reconstructed images, the method including the steps of: selecting a plurality of protocols substantially distributed across an operating range of the radiographic imaging system; imaging a phantom containing a plurality of objects over each of the protocols; computing a detectability for each object in order to determine a relative flux and contrast index set of ordered pairs for each object; determining the smallest detectable object size for each contrast set; computing a contrast index for each protocol for each contrast set; utilizing the ordered pairs of flux index and contrast index to determine an extended low contrast detectability performance function for the radiographic imaging system.

In accordance with another aspect of the disclosure and related inventions, a radiographic imaging system protocol selection reference for a radiographic imaging system of extended low contrast detectability performance data for the radiographic imaging system, the radiographic imaging system protocol selection reference is created by the steps of: selecting a plurality of protocols substantially distributed across an operating range of the radiographic imaging system; imaging a phantom containing a plurality of objects over each of the protocols; computing a detectability for each object in order to determine a relative flux and contrast index set of ordered pairs for each object; determining the smallest detectable object size for each contrast set; computing a contrast index for each protocol for each relevant contrast set, and collecting data of the ordered pairs of flux index and contrast index to provide a protocol selection reference of the extended low contrast detectability performance data for the radiographic imaging system.

In accordance with another aspect of the disclosure and related inventions, there is provided a method of selecting a protocol for a particular imaging application for a particular patient, the method comprising the steps of: obtaining an extended low contrast detectability performance data for a radiographic imaging system to be used by selecting a plurality of protocols substantially distributed across an operating range of the radiographic imaging system; imaging a phantom containing a plurality of objects over each of the protocols; computing a detectability for each object in order to determine a relative flux and contrast index set of ordered pairs for each object; determining the smallest detectable object size for each contrast set; computing a contrast index for each protocol for each relevant contrast set; utilizing the ordered pairs of flux index and contrast index to determine extended low contrast detectability performance data for the radiographic imaging system; selecting an optimized dose and contrast index by reference to the extended low contrast detectability performance data, and selecting a flux index that corresponds to the contrast index from the extended low contrast detectability performance data.

And in accordance with another aspect of the disclosure and related inventions, there is provided an extended low contrast detectability phantom which has a body having a multiplicity of diameter dimensions, at least two (2), with background material; multiple contrast sets contained within the body, each contrast set containing multiple objects of varying size, and wherein the contrast sets and the background material are arranged to satisfy the requirements of the extended low contrast detectability method.

These and other aspects of the disclosure and related inventions are further described herein with reference to the accompanying Figures.

Regarding the figures, the following designations are used to indicate color:

G=green
GR=gray
R=red
B=blue
P=purple
O=orange
T=turquoise
DG=dark green
M=magenta When referred to in the specification, the full name of each color is used to avoid confusion. In the figures, "ExLCD Contrast Performance Curve" or "Contrast Performance Curve" may be used in place of "ExLCD Performance Function."

DETAILED DESCRIPTION OF PREFERRED AND ALTERNATE EMBODIMENTS

Figure 1:
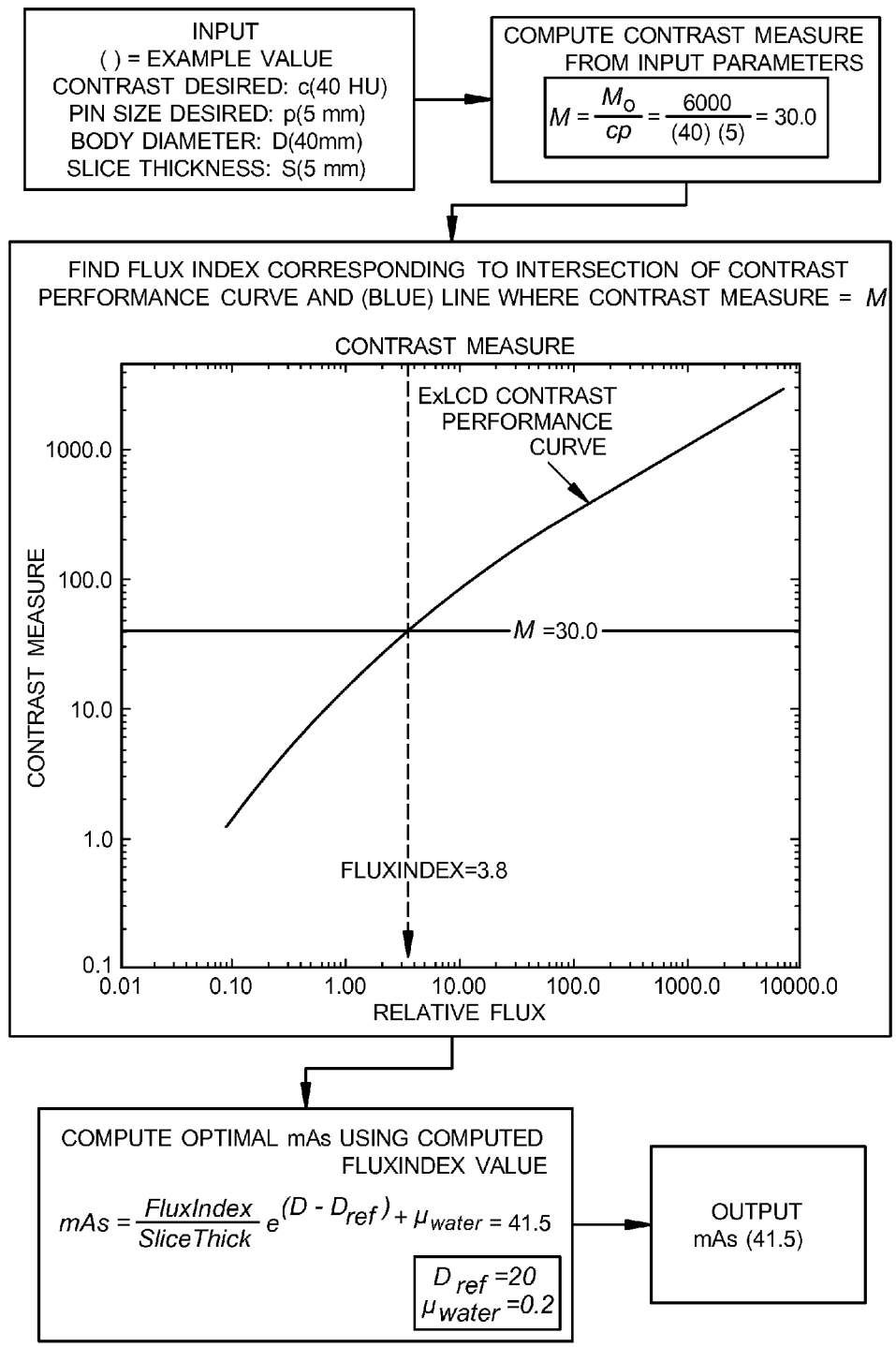
FIG. 1 is an example of data flow for Optimal Protocol selection.

FIG. 1 shows a representative data flow example for an optimal protocol selection process in accordance with the disclosure and related inventions. Assume that an ExLCD Performance Function is available for a scanner or particular radiographic imaging system. A desired contrast level is selected based on the clinical image quality requirements. In this example, the desired Contrast Index is 30.0 corresponding to a 5 mm pin at a contrast level of 40 Hounsfeld Units (HU). The Optimal Protocol Selection then determines the location on the Contrast Performance Curve corresponding to the desired Contrast Index. Since the ExLCD Performance Function is always monotonic, there will be a unique Flux Index value corresponding to the intersection of the Contrast Index value and the ExLCD Performance Function as illustrated in the graph on FIG. 1. For this example, the Flux Index value determined is 3.8. This unique Flux Index value can then be used to determine the optimal protocol.

It is assumed that the slice thickness is selected as an independent parameter. Also, it is assumed that there is a method for determining the patient body diameter D, such as the method described below for determining the patient water equivalent diameter ($D_{weq}$). For the example in FIG. 1, the patient diameter is 40 cm and the slice thickness is 5 mm resulting in a computed mAs of 41.5 as the optimal flux for the desired image quality.

Figure 29:
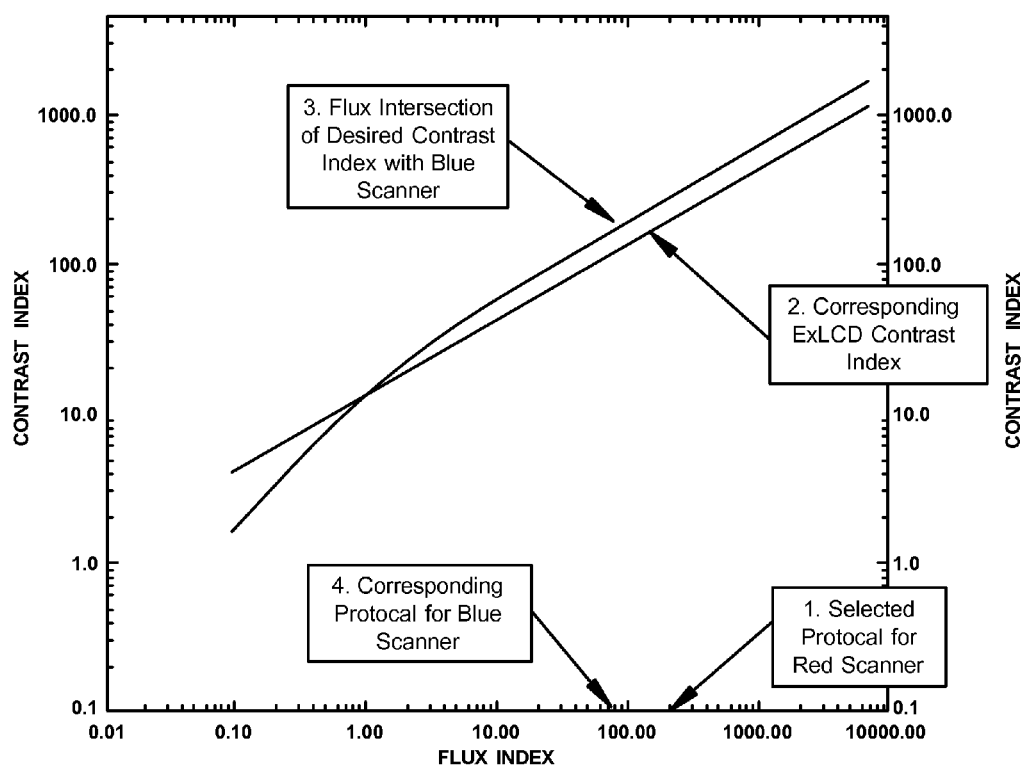
FIG. 29 is an illustration of a method for developing standardized protocols between two distinct scanners.

FIG. 29 shows a representative data flow example for standardizing clinical protocols among two or more scanners. Assuming that the "red scanner" is the baseline scanner for which protocols have been developed, this method will robustly determine corresponding clinical protocols for the "blue scanner." For each desired protocol on the red scanner, (1) determine the corresponding Flux Index for the red scanner protocol, (2) lookup the corresponding Contrast Index on the red scanner's ExLCD Performance Function, (3) find an equivalent Contrast Index value on the blue scanner's ExLCD Performance Function and (4) lookup the corresponding Flux Index based on the blue scanner's ExLCD Performance Function, thus determining an equivalent clinical protocol for the blue scanner.

Patient Water Equivalent Diameter

Figure 2:
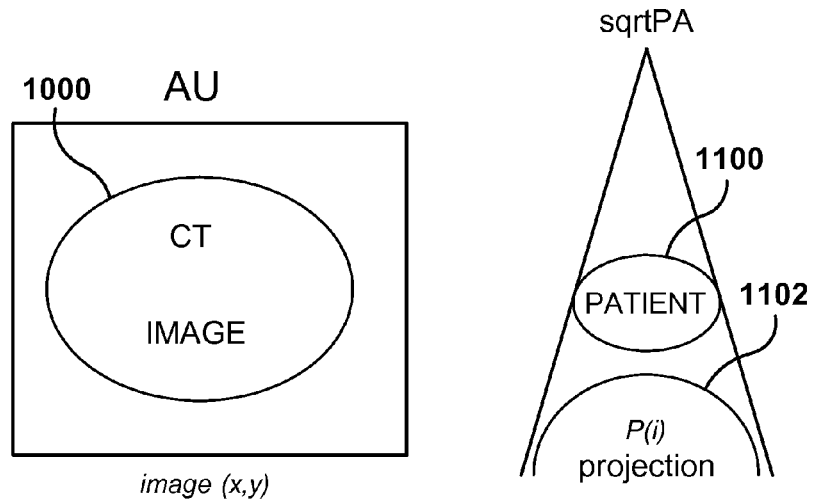
FIG. 2 is the determination of patient attenuation from image data (left) or projection data (right)
Figure 3:
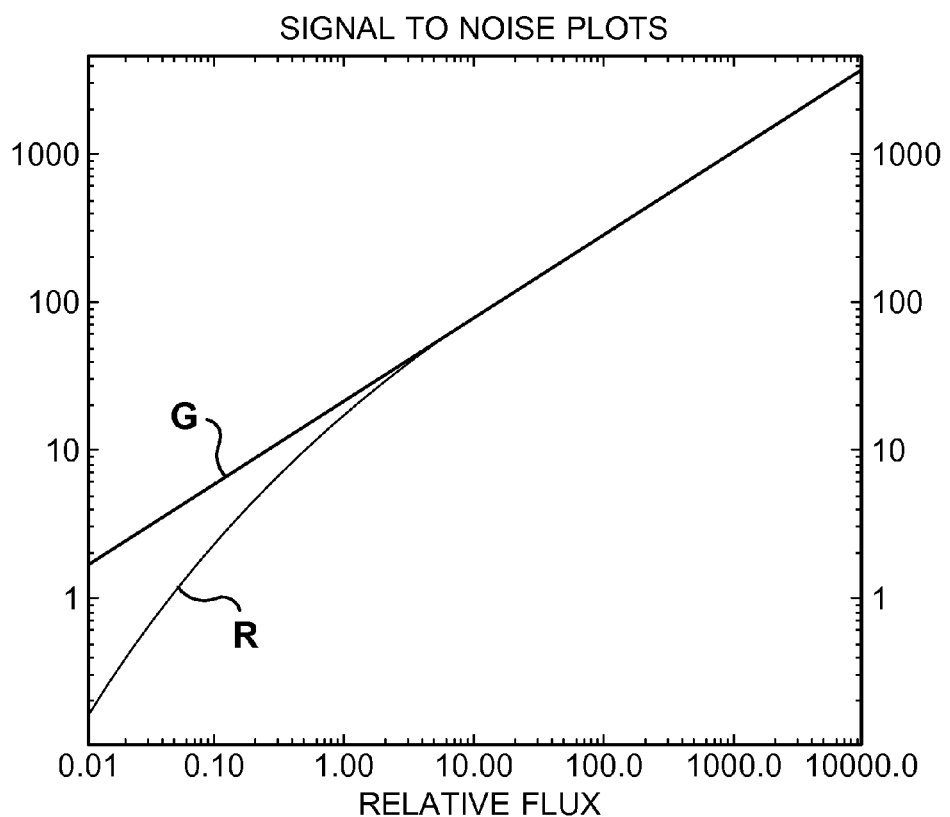
FIG. 3 is the signal-to-noise in a quantum noise limited system (green trace) and with electronic noise (red trace)
Figure 4:
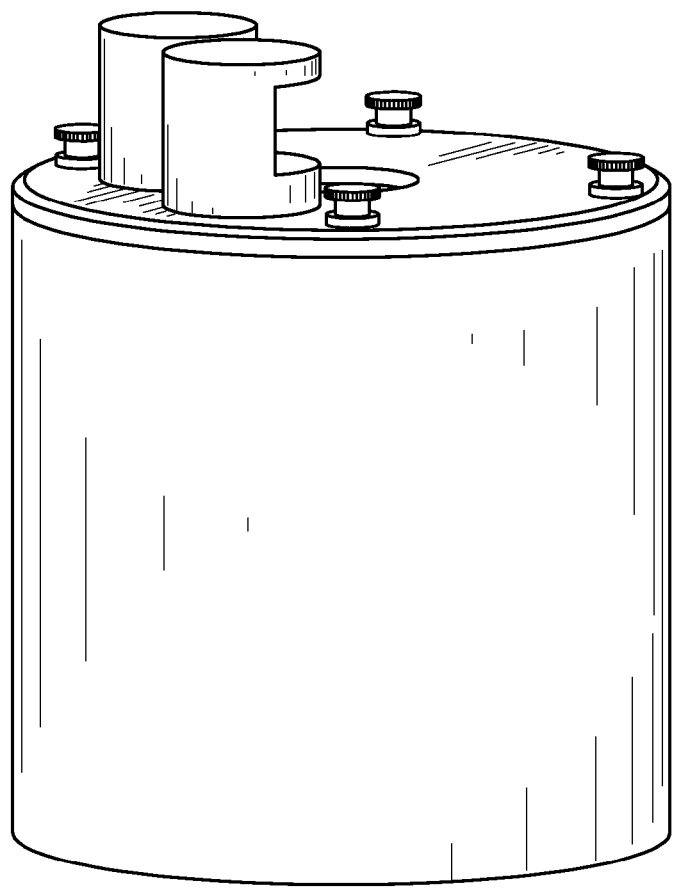
FIG. 4 is a depiction of a CATphan phantom.
Figure 5:
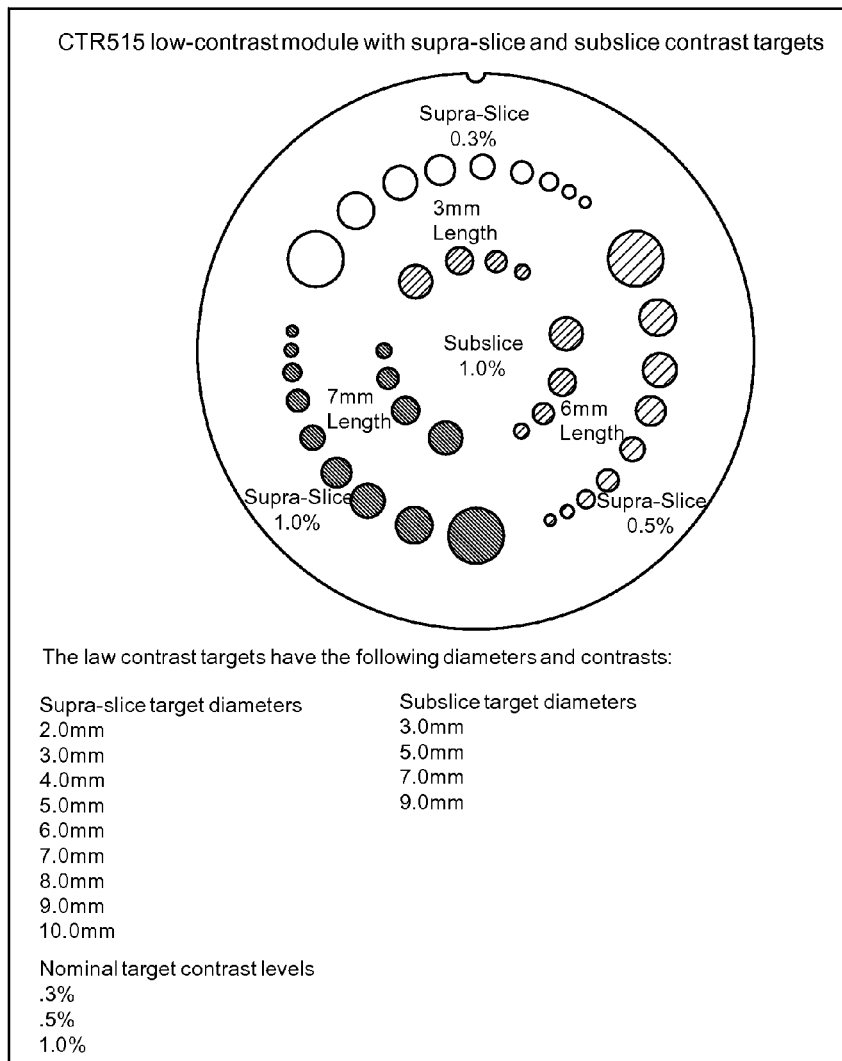
FIG. 5 is a CTP515 low contrast module drawing (left) with representative reconstructed image (right)
Figure 5:
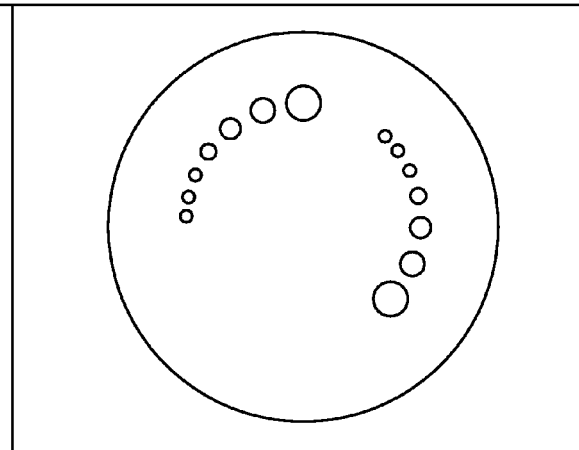
Figure 6:
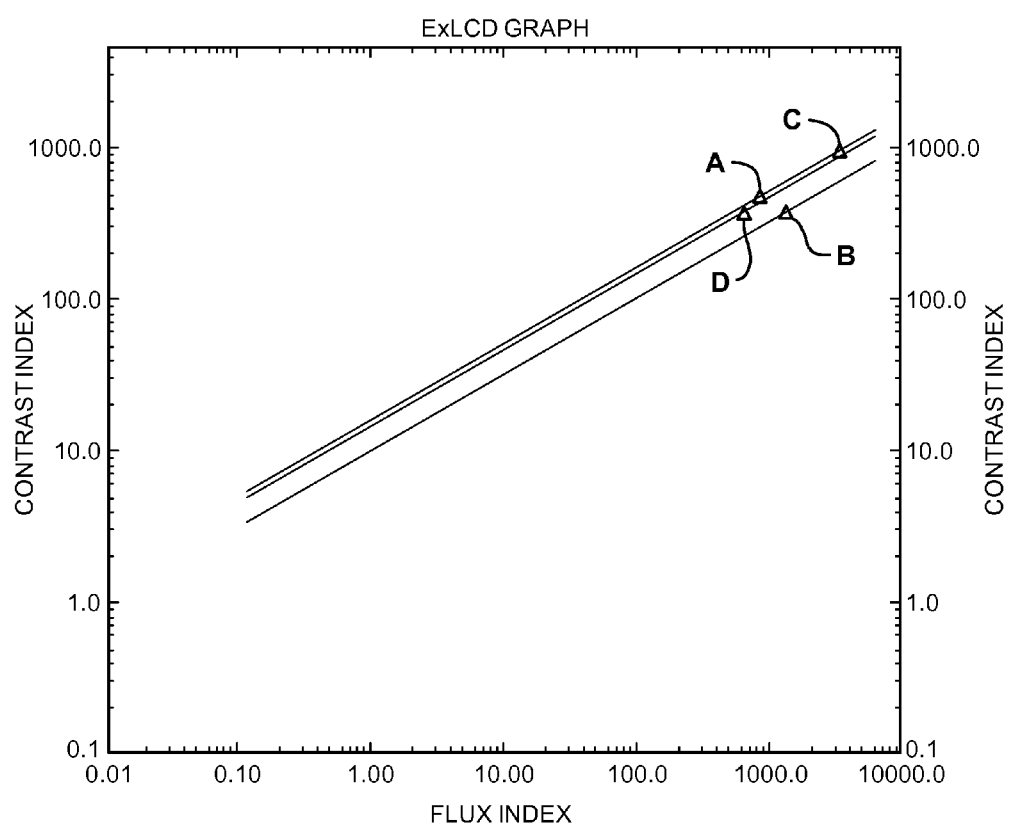
FIG. 6 is ExLCD measurements from major CT manufacturers.
Figure 7:
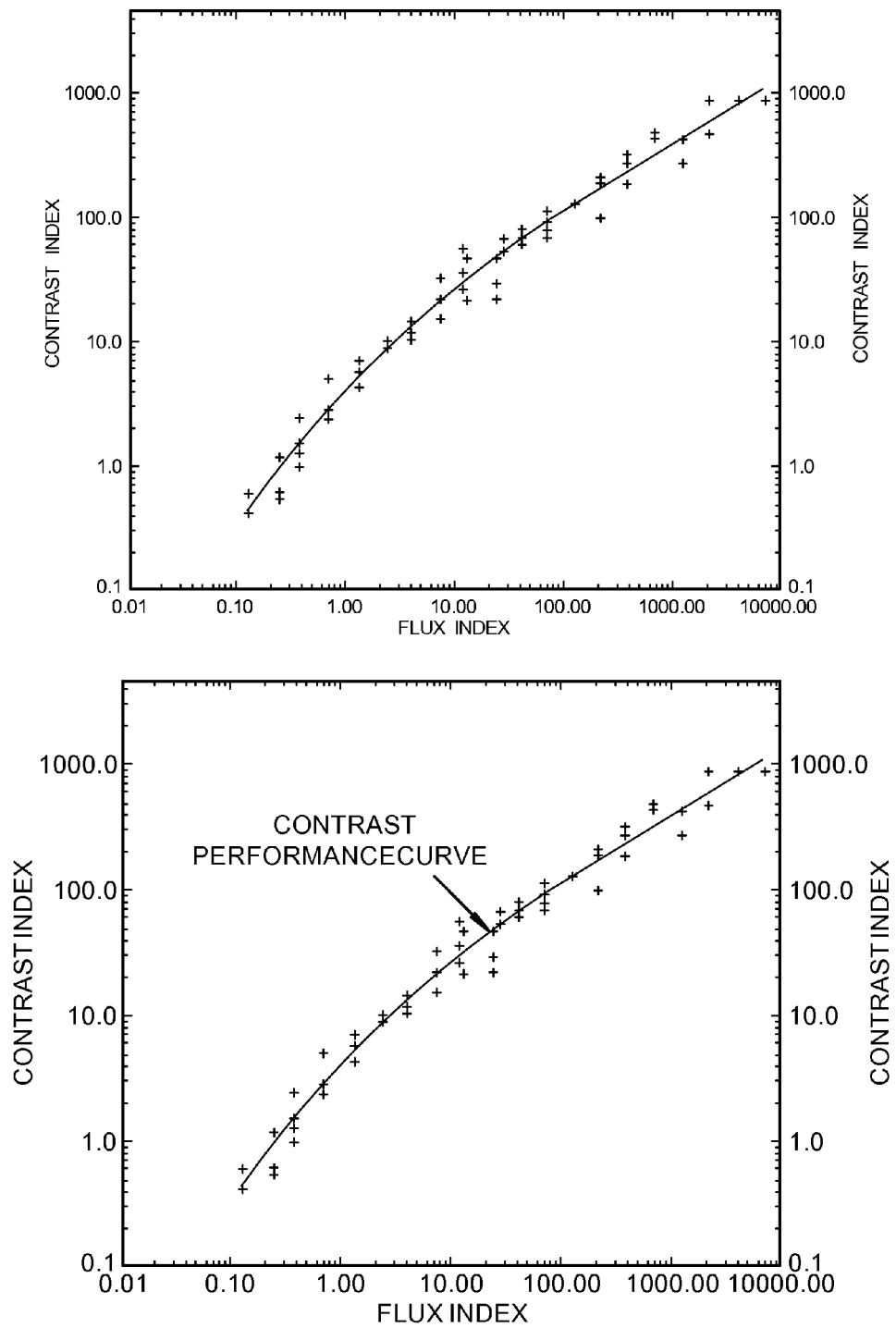
FIG. 7 is contrast measurements over the entire flux range (top) and the contrast performance curve derived from the contrast measurements (bottom)
Figure 8:
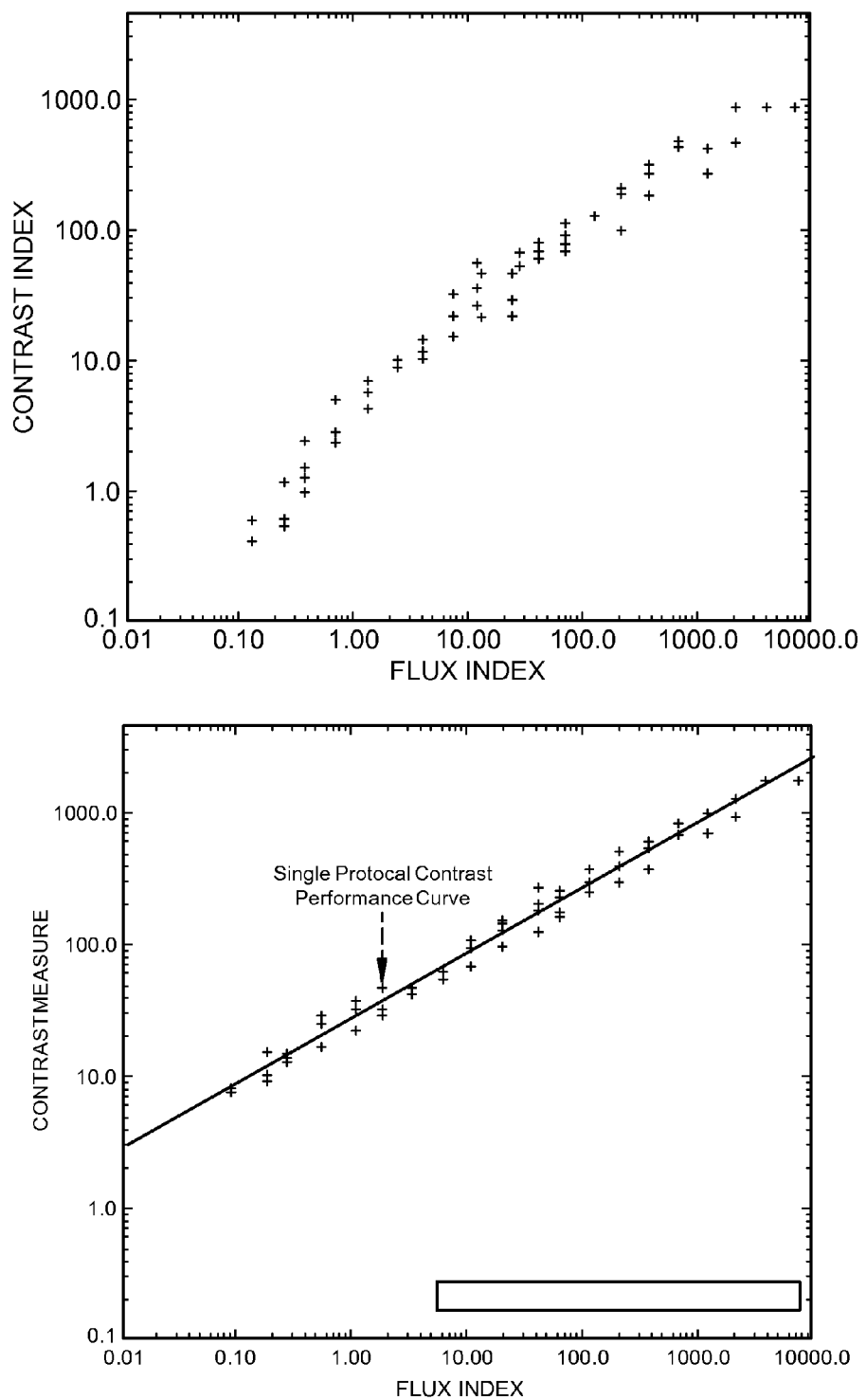
FIG. 8 (top) the Red + illustrates the single protocol measurement as is done currently vs. a multiple measurement method and (bottom) the dashed red line illustrates the assumed contrast performance curve resulting from a single protocol measurement.
Figure 9:
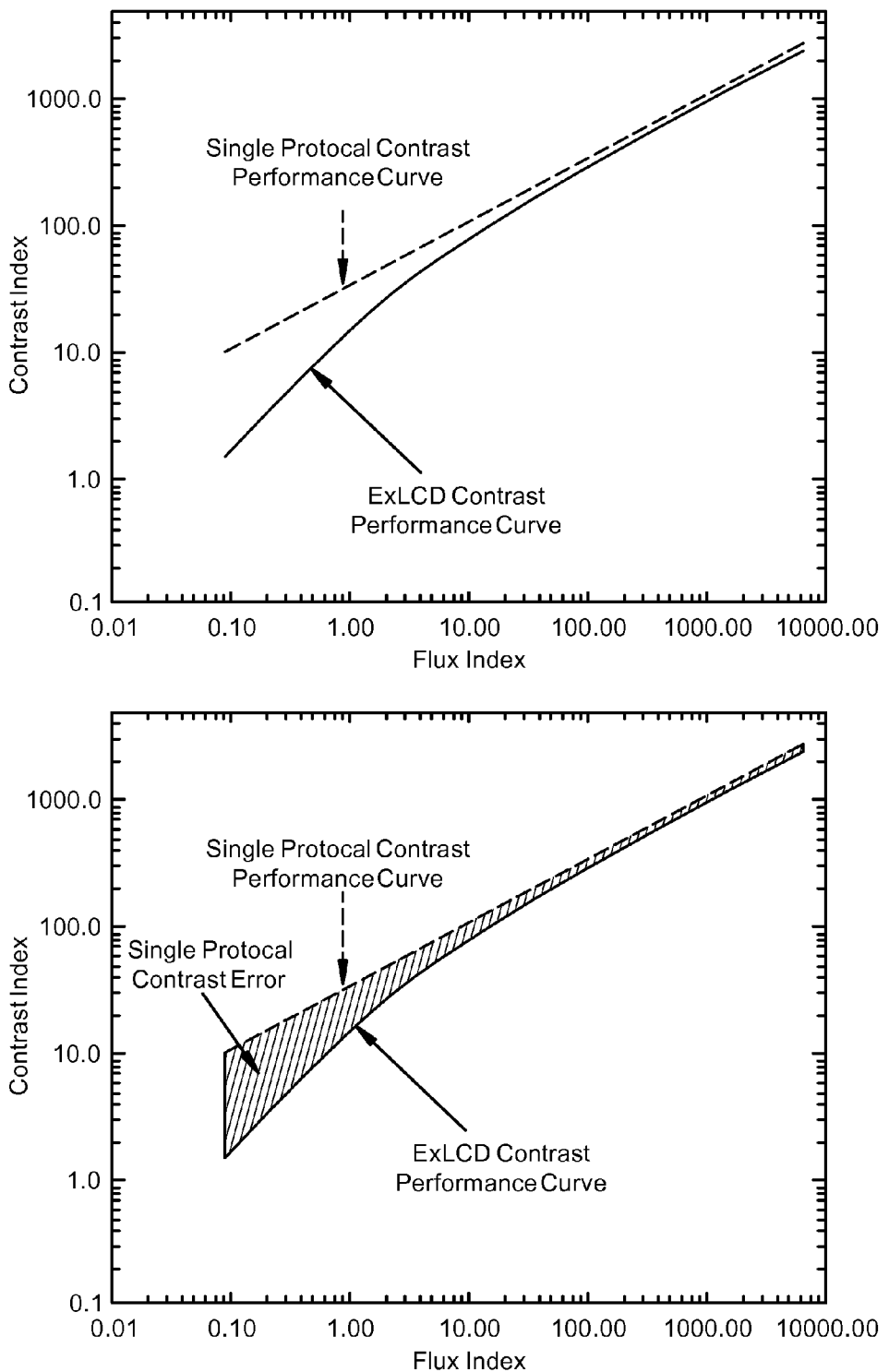
FIG. 9 is a comparison of single protocol contrast performance curve with ExLCD contrast performance curve.

The overall attenuation of a scanned object can be calculated from a CT image in terms of the water equivalent area, FIG. 2. The summation of I(x,y) is the water equivalent area where I(x,y) is obtained from the image pixels, converted to area weighted by the relative attenuation of the pixels. The square root of the water equivalent area is defined as Attenuation Units (AU).

$$D_{weq} = 2 \times \sqrt{\Sigma I(x,y)/\pi} \quad (4)$$

$$I(x,y) = (\text{image}(x,y)/100+1) \times \text{PixelArea} \quad (5)$$

Water equivalent diameter can also be estimated from a scan projection radiograph in FIG. 2 using the projection area and an appropriate scanner dependent conversion factor such as for example 0.557 for a commercially available multi-slice scanner.

$$D_{weq} = 2 \times 0.557 \times \sqrt{\Sigma P(i)/\pi} \quad (6)$$

It may also be possible to obtain patient information using the boundaries of the body shown in a radiograph. In this method, it may be important to incorporate Body Mass Index along with body diameter in order to optimize protocols.

$D_{weq}$ for the patient is used as the object diameter in Equation (7).

$$mAs = \frac{FluxIndex}{sliceThick} e^{(D_{weq}-D_{ref})*\mu_{water}} \quad (7)$$

Knowing the Flux Index, since the patient diameter $D_{weq}$ is known along with the slice thickness, the required mAs for the scan can be calculated to achieve the desired image quality for the patient.

An alternative way to determine both the object diameter and $\mu_{water}$ in Equation (7) is to use the water beam hardening corrected mean amplitude (mean of the highest 50 samples) of the scan projection radiograph from an orientation with the longest path length (usually the lateral direction). Since image noise is generally influenced by the noisiest projections, this would provide more consistent contrast performance than using $D_{weq}$ determined from the water equivalent area.

It may be that a given scanner will have more than one ExLCD Performance Function, e.g. for:
1. Slice thickness
2. X-ray beam energy (including dual energy)
3. Non-linear reconstruction This algorithm works with multiple ExLCD Performance Functions provided the corresponding protocol parameters are provided as input.

It is essential to have a method for determining the desired Contrast Index in a clinical setting. One simple method is to specify the desired object contrast differentiation in Hounsfield units and the object size. Then, the ExLCD Contrast Index can be immediately computed from Equation 1. It is expected that more sophisticated methods will be developed, for example, derived from actual clinical images. For example, clinical images from various patients at various dose levels for a particular clinical task on an ExLCD calibrated scanner are qualitatively graded by radiologists for acceptability, ExLCD is then used to determine the contrast index for each patient image. In this way clinical opinions can be associated with the ExLCD performance relationship. A sufficient number of qualitative radiologist studies regarding clinical acceptability will eventually reveal the appropriate contrast index to use in clinical practice. ExLCD provides the method to duplicate the required results for any patient on any calibrated scanner.

It is advantageous from the standpoint of possible patient side effects to use the smallest possible concentration of contrast media, however, it is critical to use enough contrast so that the desired image quality can be achieved. The ExLCD method can be expanded to optimize the concentration of contrast media used for a radiographic imaging system.

It is necessary to measure the reconstructed object contrast in order to track contrast performance impacted by non-linear or iterative reconstruction. Therefore, the actual reconstructed contrast will be measured in the ExLCD method. Using measured contrast, a reconstruction process with a highly filtered noise spectrum will cause object smoothing that will result in a lower ExLCD Contrast Index than a reconstruction process that is able to filter the noise while retaining the spatial geometry of the original object.

Figure 13:
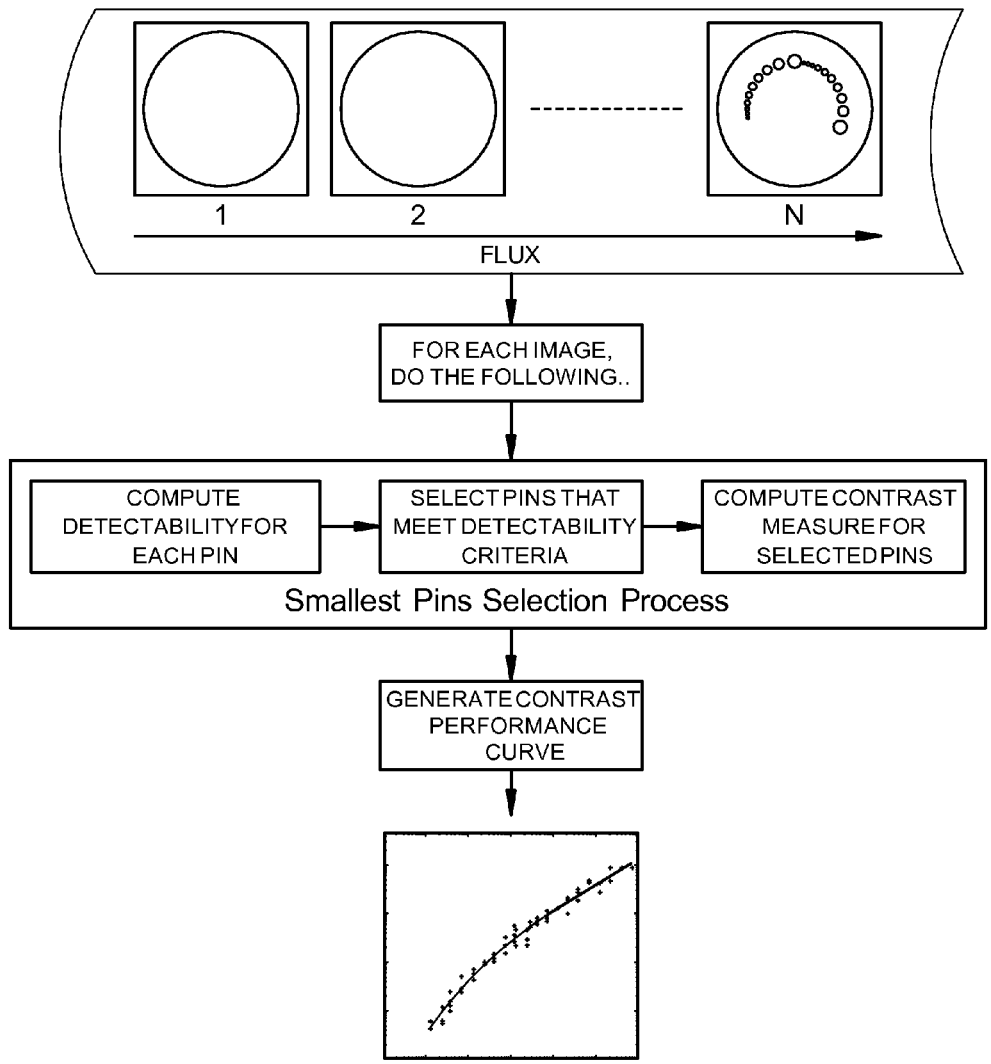
FIG. 13 is a block diagram of the ExLCD method.

The ExLCD method of the disclosure can be partitioned into four main components that are illustrated in the block diagram in FIG. 13: (1) the ExLCD phantom containing various contrast/diameter cross-sections, (2) the set of scan protocols and image slices used for ExLCD measurement, (3)

the detectability determination, (4) the Contrast Index function generator and parameter calculation.

As used herein, the terms "extended low contrast detectability" and "ExLCD" mean and refer to a universal performance relationship for a radiographic imaging system that provides numeric LCD values (Contrast Index) over a range operating conditions and patient sizes (Flux Index). The terms "extended low contrast detectability function", "ExLCD function" and "ExLCD performance function" and "ExLCD performance curve" and "Contrast Performance Curve" mean and refer to any data or tangible representation of the Contrast Index vs. Flux Index relationship.

As used herein, a Flux Index value is defined for each protocol variation within a core operating mode to incorporate those protocol parameters that directly affect the x-ray flux available for detection or image performance reconstruction parameters. The Flux Index value is "relative" to the core operating mode. That is, a Flux Index value for one core operating mode cannot be directly compared to a Flux Index value for another core operating mode. This relative Flux Index value, for a specific core operating mode, is any expression that is proportional to the x-ray flux available for detection. For a CT scanner, one possible definition is given by Equation 3 and the accompanying descriptions.

As used herein, a Contrast Index value is defined by Equation 1 and its accompanying descriptions. It is determined by measurement and calculation for each protocol within any core operating mode and each relevant contrast set. For a given core operating mode, each set of contrast objects can be assigned a nominal contrast level, c. That contrast level is set by the manufacturing characteristics of the phantom as determined by the phantom design and the phantom calibration done for the core operating mode. The smallest object size detectable, p, is then determined for each protocol within the core operating mode. As described elsewhere, the ExLCD algorithm determines a detectability value for each object size in the contrast set by examining the image(s) produced for that protocol and then determining the smallest object size, p, that corresponds to a detectability value that is greater than or equal to the detectability threshold.

A contrast set is relevant for a given set of protocol parameters, if either some, but not all objects in the set are detectable, or when all objects in the contrast set are detectable or no objects in the contrast set are detectable. A smallest detectable object size can be reliably inferred by extrapolation or interpolation from the detectability measures of the objects in the contrast set.

In accordance with the disclosure, there may be performed multiple calibrations for a given radiographic imaging system. For example, a complete ExLCD Scanner Characterization includes the following elements:
1. A new ExLCD Calibration is done for each core operating mode. The core operating mode changes when changes are made in core operating parameters, e.g.
   a. X-ray tube energy
   b. Source filter and collimator
   c. Reconstruction mode, e.g. non-linear reconstruction
2. Up-to-date dose measurement
3. Calibration of the ExLCD Phantom to compensate for manufacturing tolerances and scanner spectral characteristics As referred to herein, an ExLCD performance curve or ExLCD performance functions is one form or format of an output of the ExLCD algorithm for any core operating mode for the radiographic imaging system. The ExLCD performance curve embodies the relation between the Flux Index and the Contrast Index over the range of the Flux Index for that core operating mode. It may be represented as an array of Flux Index and Contrast Index values or by other appropriate parameterization. The relation is embodied in a manner that provides the (on-line) capability to determine a Contrast Index for any desired Flux Index or conversely to determine the protocol parameters for any desired Contrast Index and any patient size.

As referred to herein, a radiographic imaging system is any imaging system that relies on electromagnetic radiation (x-ray, gamma ray, etc.) for building the image. For application of the described ExLCD system and methods, radiographic imaging systems include but are not limited to CT scanners, digital radiographic devices, mammography devices, nuclear imaging devices, SPECT devices.

As referred to herein, the various detection methods include a system of phantom images and methods designed to ascertain the quality of an image interpretation task. Some of the detectability methods include the following or combinations of the following: human opinions of object visual quality in fixed object phantoms (poorest of methods), human task based observations regarding how accurately the presence or absence of an object in an image can be determined (forced alternative choice methods for example), statistical noise analysis methods where the detectability of an object is inferred using some measure of image noise, matched filter methods where the object spatial frequencies are determined and then used to analyze the noise within those spatial frequencies, an ideal Bayesian Observer signal to noise analysis, a Non Pre-whitening Matched Filter signal to noise ratio (NPWMFSNR), etc., as further described for example by the International Commission on Radiation Units and Measurements (ICRU) Report 54 "Medical Imaging—The Assessment of Image Quality", incorporated herein by reference. The NPWMFSNR has been found to most closely represent objective human task based assessments. The NPWMFSNR is therefore the preferred choice for the ExLCD detection method although other methods could be employed. A variation of the NPWMFSNR is to measure the reduction in contrast of the object due to the MTF of the system such that systems that reduce the spatial frequencies of the noise but retain the spatial frequencies of the input object will score a higher NPWMFSNR.

Dual Energy

The concepts of ExLCD as disclosed herein can be applied to energy discriminating radiographic imaging the same as for energy integrating imaging with some special considerations. The objects within the phantom must be made of energy sensitive materials such as Calcium Hydroxyapatite. The phantom objects would use various percentages of the energy sensitive material. The concept is to build concentration sets of energy sensitive material objects. This would make the phantom objects sensitive to the energy discrimination acquisition and reconstruction methods employed by the radiological imaging device. Energy discriminating systems can provide various types of images. Among these for dual energy CT are: high kV and low kV images that are comparable to conventional images; a set of basis material images such as a calcium image and water image (if the basis materials chosen are calcium and water); and monochromatic images at a selected keV that are produced by an appropriate combination of data from the basis material images or basis material projection data. Any one or all of these images could be evaluated with ExLCD using an energy sensitive phantom.

ExLCD Phantom

The ExLCD phantom must support making contrast measurements over the flux range. A phantom diameter of 20 cm, similar to the current CATphan will support flux values at the high flux end of the desired range but will not support the lowest flux range values. Therefore, a second phantom diameter of 40 cm is provided that will, with appropriate scan parameters, achieve the lowest flux values in the desired range.

When the detected flux is at the lower end of the desired range, the contrast levels in the current CATphan will not be seen. Therefore, additional contrast sets are introduced to be detectable in the low flux ranges.

Figure 14:
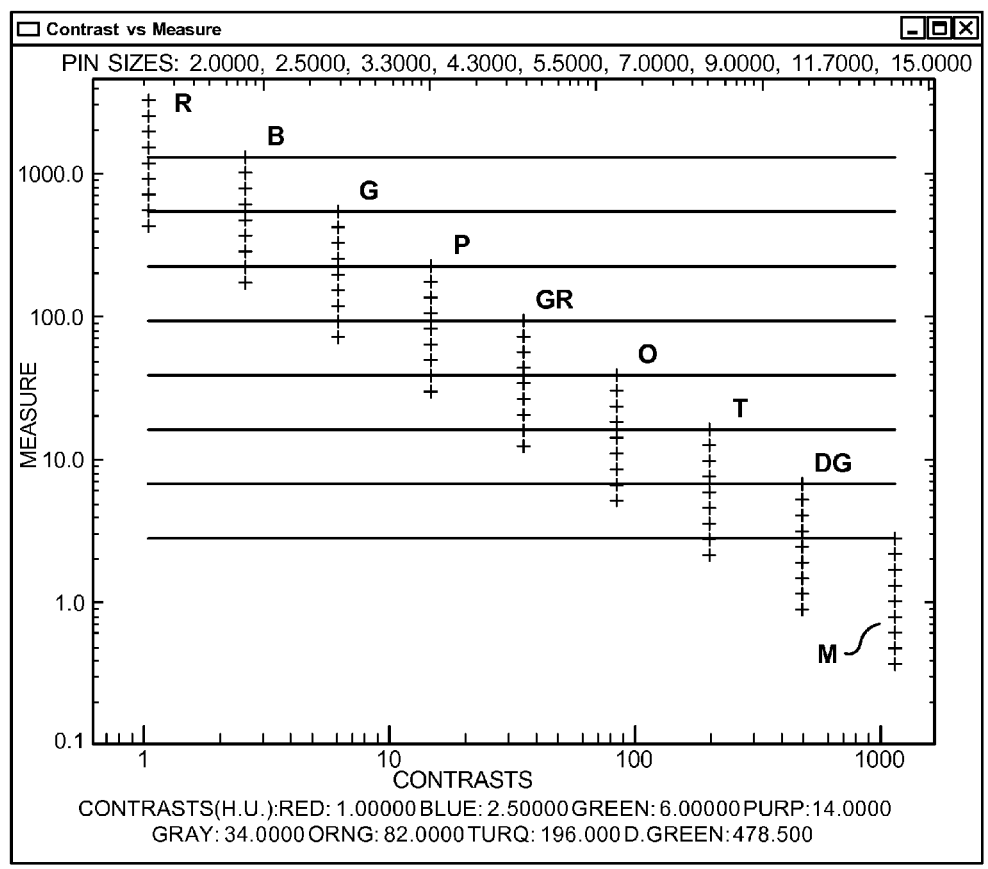
FIG. 14 is a pin size sampling and contrast set sampling wherein each color represents a distinct contrast set and contrast sets are interleaved (dotted lines) with the smallest pin of any contrast set positioned between the $4^{th}$ and $5^{th}$ pins of the next lower contrast level.

The ExLCD phantom contains 9 distinct contrast sets. Each contrast set contains 9 objects, sometimes referred to as "pins". The pin sizes are chosen to generate uniform samples along the logarithmic contrast level axis as shown in FIG. 14. The uniform samples being derived by the following formulation:

Let the number of samples be N, and $V_1$ and $V_N$ be the first and last elements.

ramp=1, 2, 3 ... N $V_1$ and $V_N$ can be written as:

$$V_1 = a^{b+1}$$

$$V_N = a^{b+N}$$

$$b + 1 = \log_a(V_1) = \frac{\ln(V_1)}{\ln(a)} \quad (1)$$

$$\text{Similarly, } b + N = \log_a(V_N) = \frac{\ln(V_N)}{\ln(a)} \quad (2)$$

Solving equations 1 and 2, we get:

$$a = e^{\left(\frac{\ln(V_N) - \ln(V_1)}{N-1}\right)}$$

$$b = \frac{\ln(V_1)}{\ln(a)} - 1$$

Hence the equally sampled Vec can be defined as $$vec = a^{(b+ramp)}$$

The contrast sets are designed so that the sampling rate along the logarithmic contrast level axis is effectively doubled. That is, contrast sets are interleaved as illustrated by the dotted lines in the graph. Specifically, the smallest pin of any contrast set (except the set with the lowest contrast value) is positioned between the $4^{th}$ and $5^{th}$ pins of the contrast set with the next lower contrast value.

The specific pin sizes and specific contrast level values are shown in Table 2. For each contrast level, there is an indication of whether that contrast level is required with the 20 cm diameter, the 40 cm diameter or both.

Figure 15:
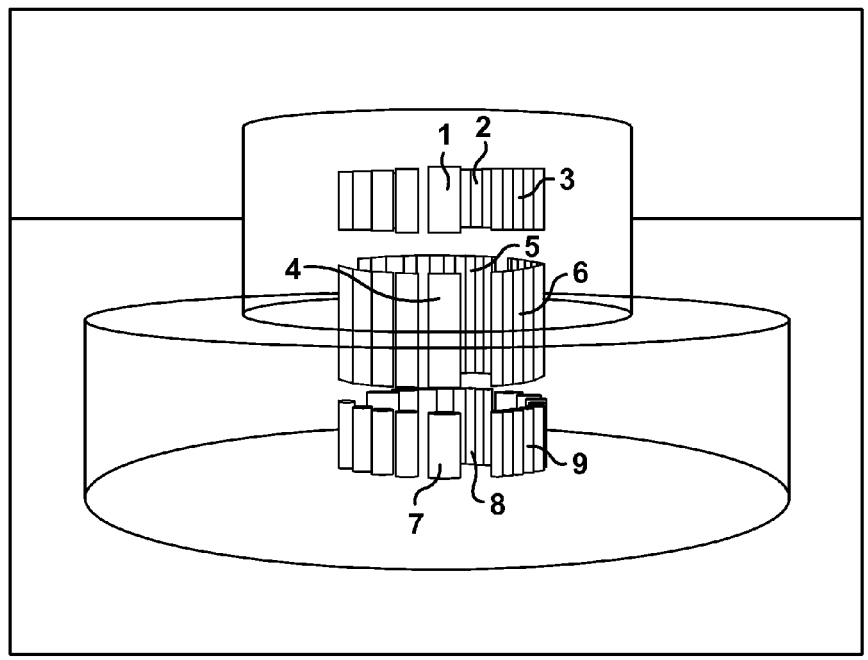
FIG. 15 is an ExLCD phantom configuration showing two distinct diameters and 9 distinct contrast sets.

Based on Table 2 the phantom can be configured as illustrated in FIG. 15. The varying contrast levels are depicted by various shaded and/or numbered pegs indicated by reference numerals 1 through 9, positioned longitudinally inside the phantom. In the drawing, the middle three contrast sets, indicated at reference numerals 4, 5 and 6, are positioned so that they can be used with both of the two diameters.

Figure 16:
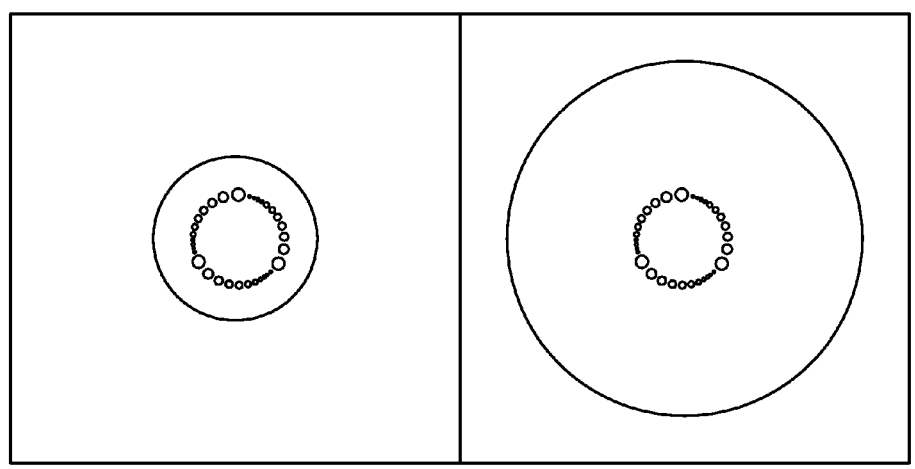
FIG. 16 are cross-sections of the ExLCD (simulated) phantom showing a 20 cm cross-section (left) and a 40 cm cross-section (right)

Representative cross-sections are shown in FIG. 16. The image on the left illustrates a 20 cm diameter cross-section; the image on the right illustrates a 40 cm diameter cross-section. The phantom will be designed so that there will be multiple slices with the same cross-section and contrast set. By combining the measurements from the multiple slices, a more accurate measurement of the actual contrast of the reconstructed object will be possible.

Additionally, the phantom must have regions in which the noise standard deviation and the noise power spectrum can be measured. The phantom may also need a region and object that will support measuring the system MTF.

Figure 31:
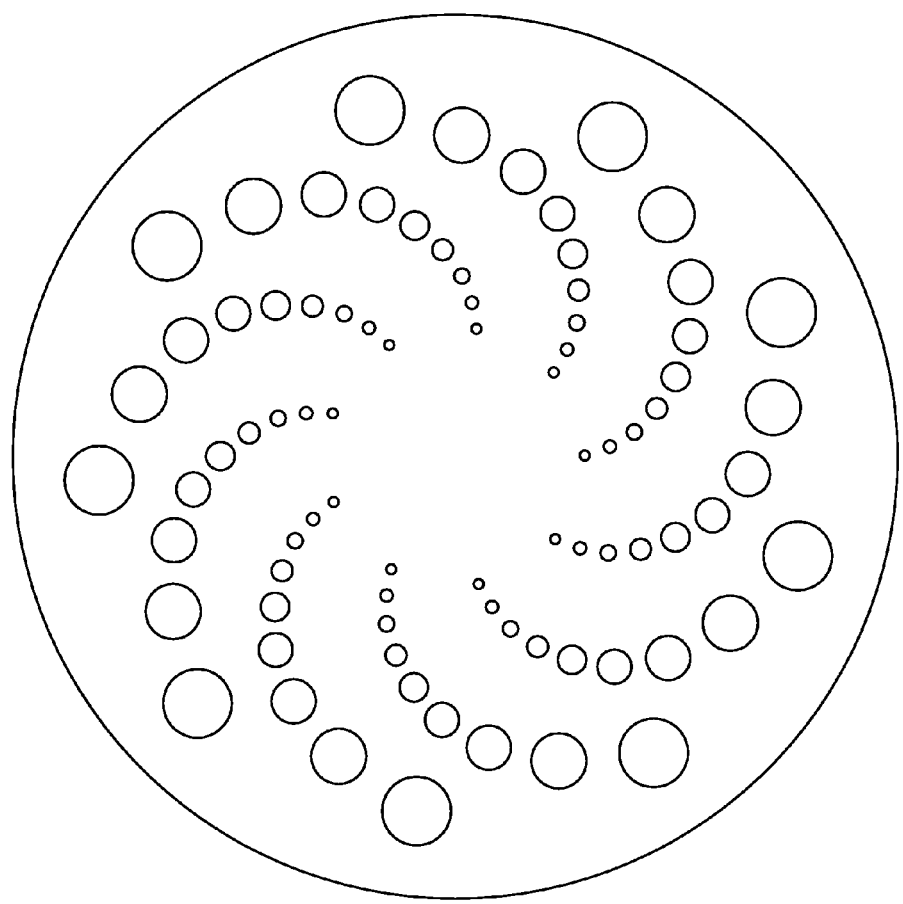
FIG. 31 is a two-dimensional cross-section of alternative embodiments of an ExLCD phantom.
Figure 32:
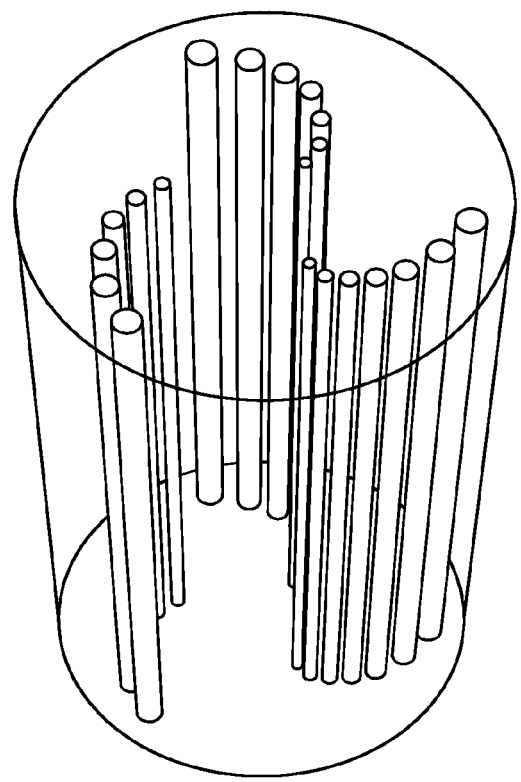
FIG. 32 are three-dimensional depictions of two alternative embodiments of an ExLCD phantom with only three of nine contrast levels being used; the upper diagram has cylindrical objects and in the lower diagram, the centers of the objects in any horizontal 2D cross-section trace out helices.
Figure 32:
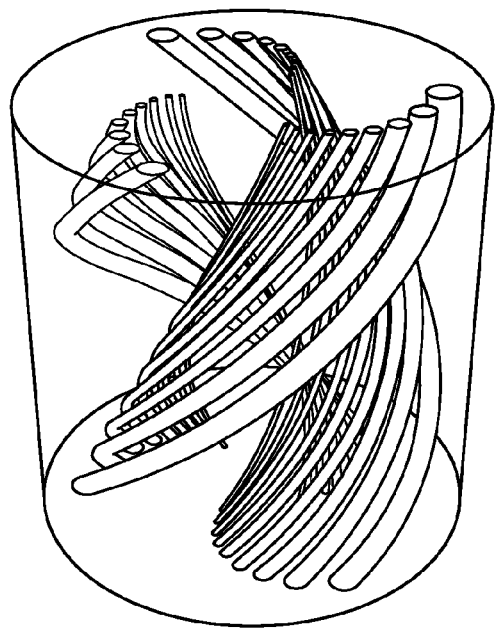

The specific design described in this document is one of many designs that can achieve the measurement objectives. Two alternative embodiments of an ExLCD phantom will have the cross-section illustrated in FIG. 31. In this figure, each color or shade represents a different contrast level. In this embodiment, all contrast levels and pin sizes appear in each cross-section. In using this design, the noise response in the reconstruction as a function of radius will need to be incorporated. FIG. 32 illustrates two embodiments sharing the cross-section shown in FIG. 31. In both depictions, for clarity only three of nine contrast sets are shown. The phantom depicted in the upper half of FIG. 32 consists of cylindrical objects. The phantom pins provide consistent objects from slice to slice that are not unlike a representation of axially oriented vessels in a patient. This provides a means to test non-linear reconstruction processing that may take advantage of slice to slice consistency. The phantom depicted in the lower half of FIG. 32 is also composed of objects which are helical cylinders. That is, for each object, the centers of the circular profiles in the horizontal two-dimensional cross-sections form a helix. This serves to reduce the coherence between slices and can be used to calibrate performance when slice to slice variation is present. This provides a means to test non-linear and iterative reconstruction processing that may take advantage of slice to slice consistency. Either phantom can be used with a 20 cm or 40 cm diameter, as shown in FIG. 15.

ExLCD Protocols

There are 20 distinct protocol samples, here selected between 0.09 and 7,200.0, uniformly distributed on the logarithmic relative flux axis. The specific values for relative flux are shown in Table 3 along with the corresponding scan parameters and phantom diameter.

TABLE 2

Pin size values and contrast level values.

|  | 1 | 2 | 3 | 4 | 5 | 6 | 7 | 8 | 9 |
|---|---|---|---|---|---|---|---|---|---|
| Pin Sizes (mm) | 2.00 | 2.57 | 3.31 | 4.26 | 5.48 | 7.05 | 9.06 | 11.66 | 15.00 |
| Contrast Set # |  | 1 |  |  | 2 |  |  | 3 |  |
| Contrast Levels (HU) | 1.00 | 2.41 | 5.83 | 14.08 | 33.99 | 82.07 | 198.17 | 478.49 | 1155.35 |
| Used with 20 cm Diameter | ✓ | ✓ | ✓ | ✓ | ✓ | ✓ |  |  |  |
| Used with 40 cm Diameter |  |  |  | ✓ | ✓ | ✓ | ✓ | ✓ | ✓ |

TABLE 3

Relative flux values for selected protocols

| # | Relative Flux | mAs | Slice Thickness (mm) | Diameter (cm) |
|---|---|---|---|---|
| 1 | 0.092 | 5 | 1 | 40 |
| 2 | 0.183 | 10 | 1 | 40 |
| 3 | 0.275 | 15 | 1 | 40 |
| 4 | 0.549 | 30 | 1 | 40 |
| 5 | 1.099 | 60 | 1 | 40 |
| 6 | 1.832 | 100 | 1 | 40 |
| 7 | 3.297 | 90 | 2 | 40 |
| 8 | 6.044 | 110 | 3 | 40 |
| 9 | 10.989 | 200 | 3 | 40 |
| 10 | 19.781 | 360 | 3 | 40 |
| 11 | 36.631 | 400 | 5 | 40 |
| 12 | 63.006 | 430 | 8 | 40 |
| 13 | 60.000 | 60 | 1 | 20 |
| 14 | 40.000 | 20 | 2 | 20 |
| 15 | 20.000 | 20 | 1 | 20 |
| 16 | 10.000 | 10 | 1 | 20 |
| 17 | 115.000 | 115 | 1 | 20 |
| 18 | 200.000 | 200 | 1 | 20 |
| 19 | 360.000 | 360 | 1 | 20 |
| 20 | 660.000 | 330 | 2 | 20 |
| 21 | 1200.000 | 150 | 8 | 20 |
| 22 | 2160.000 | 270 | 8 | 20 |
| 23 | 3840.000 | 480 | 8 | 20 |
| 24 | 7200.000 | 900 | 8 | 20 |

Figure 17:
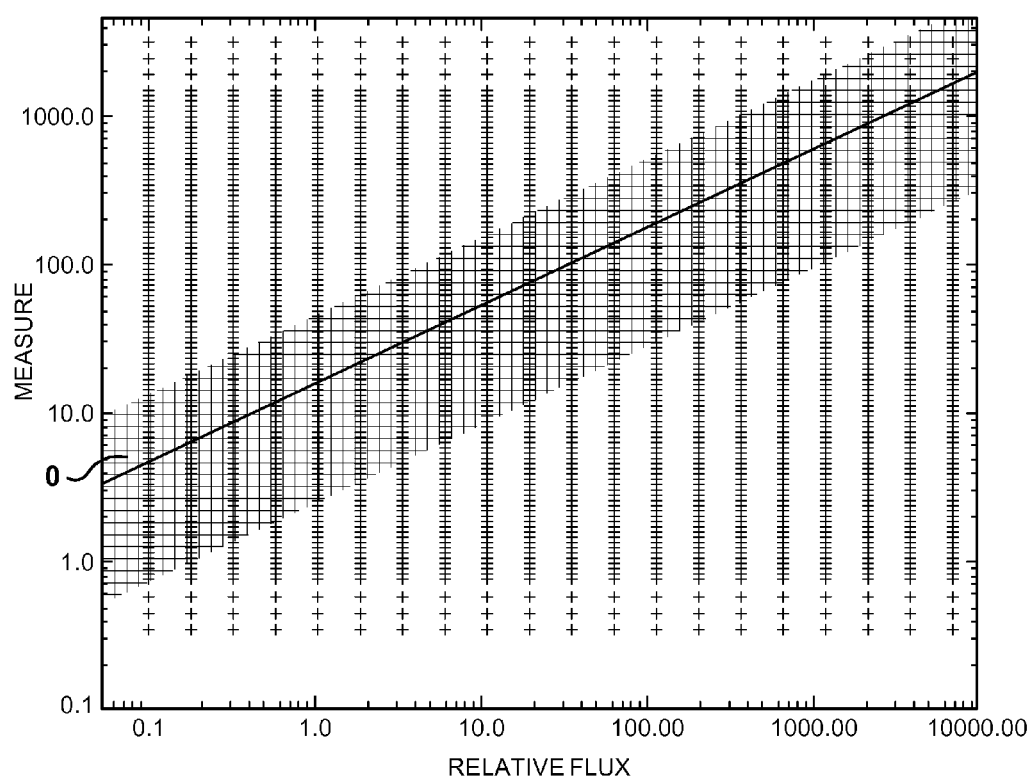
FIG. 17 are contrast sets represented at each protocol wherein the orange region represents the approximate required coverage.

There are 12 distinct slices (cross-sections) of the ExLCD phantom as shown by the number of check marks (✓). Theoretically, each of those 12 slices could be scanned for each of the 20 protocols resulting in 240 image slices. Examination of FIG. 17 however, illustrates that only a relatively small subset of the 240 possible image slices is relevant. The shaded region in the figure represents the approximate coverage that is required, or in other words the relevant contrast sets. Slice thicknesses will need to be measured to accurately determine the Flux Index, since there can be considerable differences between the nominal selected slice and the true slice sensitivity profile.

Based on this analysis, 44 image slices were included in the ExLCD measurement process shown in Table 4.

TABLE 4

Image slices selected for ExLCD measurement processing.

| # | Relative Flux | mAs | Slice Thickness (mm) | Diameter (cm) | Contrast Set |
|---|---|---|---|---|---|
| 1 | 0.092 | 5 | 1 | 40 | 2 |
| 2 | 0.183 | 10 | 1 | 40 | 2 |
| 3 | 0.275 | 15 | 1 | 40 | 2 |
| 4 | 0.549 | 30 | 1 | 40 | 2 |
| 5 | 1.099 | 60 | 1 | 40 | 2 |
| 6 | 1.832 | 100 | 1 | 40 | 2 |
| 7 | 3.297 | 90 | 2 | 40 | 2 |
| 8 | 6.044 | 110 | 3 | 40 | 2 |
| 9 | 0.092 | 5 | 1 | 40 | 3 |
| 10 | 0.183 | 10 | 1 | 40 | 3 |
| 11 | 0.275 | 15 | 1 | 40 | 3 |
| 12 | 0.549 | 30 | 1 | 40 | 3 |
| 13 | 1.099 | 60 | 1 | 40 | 3 |
| 14 | 1.832 | 100 | 1 | 40 | 3 |
| 15 | 3.297 | 90 | 2 | 40 | 3 |
| 16 | 6.044 | 110 | 3 | 40 | 3 |
| 17 | 10.989 | 200 | 3 | 40 | 1 |
| 18 | 19.781 | 360 | 3 | 40 | 1 |
| 19 | 36.631 | 400 | 5 | 40 | 1 |
| 20 | 63.006 | 430 | 8 | 40 | 1 |
| 21 | 60.000 | 60 | 1 | 20 | 1 |
| 22 | 40.000 | 20 | 2 | 20 | 1 |
| 23 | 20.000 | 20 | 1 | 20 | 1 |
| 24 | 10.000 | 10 | 1 | 20 | 1 |
| 25 | 10.989 | 200 | 3 | 40 | 2 |
| 26 | 19.781 | 360 | 3 | 40 | 2 |
| 27 | 36.631 | 400 | 5 | 40 | 2 |
| 28 | 63.006 | 430 | 8 | 40 | 2 |
| 29 | 60.000 | 60 | 1 | 20 | 2 |
| 30 | 40.000 | 20 | 2 | 20 | 2 |
| 31 | 20.000 | 20 | 1 | 20 | 2 |
| 32 | 10.000 | 10 | 1 | 20 | 2 |
| 33 | 115.000 | 115 | 1 | 20 | 1 |
| 34 | 200.000 | 200 | 1 | 20 | 1 |
| 35 | 360.000 | 360 | 1 | 20 | 1 |
| 36 | 660.000 | 330 | 2 | 20 | 1 |
| 37 | 1200.000 | 150 | 8 | 20 | 1 |
| 38 | 2160.000 | 270 | 8 | 20 | 1 |
| 39 | 3840.000 | 480 | 8 | 20 | 1 |
| 40 | 7200.000 | 900 | 8 | 20 | 1 |
| 41 | 115.000 | 115 | 1 | 20 | 2 |
| 42 | 200.000 | 200 | 1 | 20 | 2 |
| 43 | 360.000 | 360 | 1 | 20 | 2 |
| 44 | 660.000 | 330 | 2 | 20 | 2 |

EXLCD Algorithm

The ExLCD detectability method includes one or more of the detection methods listed above along with the capability to incorporate actual measured contrast. The pin image contrast can be measured as follows:
 1. Calibrate the phantom to determine the effective mean contrast of the pins.
 2. Use the calibrated phantom images to define a map of the pixel locations within the geometric area of each pin.
 3. Use the pin area maps to measure the average contrast for each test condition.
 4. Average the value from multiple slices that are identical in their geometry and contrast set.

Figure 18:
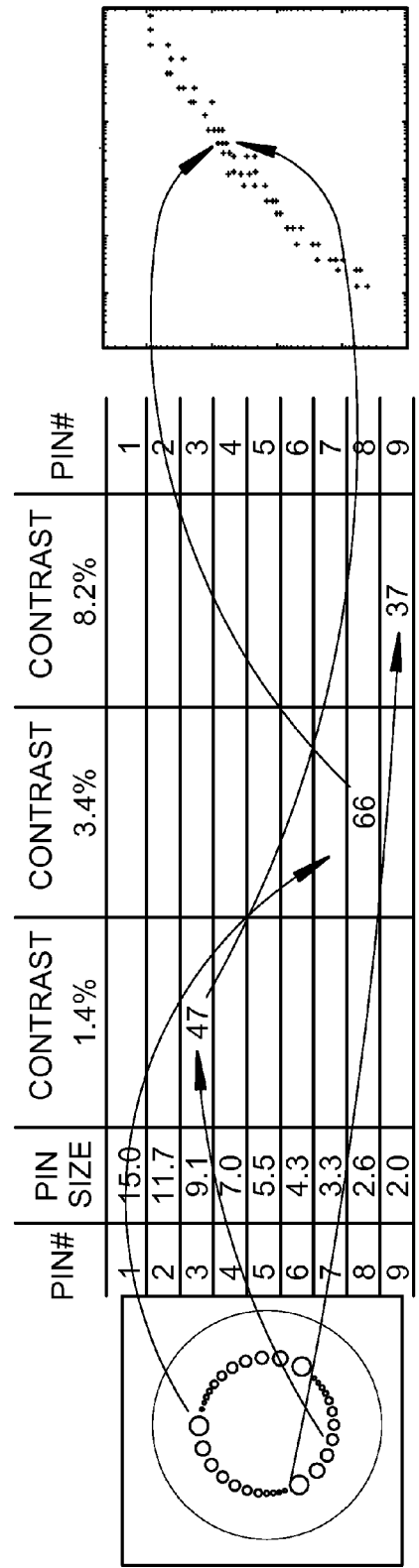
FIG. 18 is an illustration of a visibility mapping wherein pins are numbered 1-9 from largest to smallest.

FIG. 18 illustrates the result of the detectability determination for the reconstructed image slice described as Test 32 in Table 4. The smallest pins detectable in each of three contrast sets are identified as indicated in the chart. Based on the identified pin numbers, the corresponding pin sizes and the associated contrast level are the raw data for the measurement for that reconstructed image.

For example, in FIG. 18, three ExLCD contrast measurements may be recorded using the definition in Equation 1.

$$\left[\frac{6000}{9.06*14}, \frac{6000}{2.56*34}, \frac{6000}{2.0*82}\right] = [47, 69, 37] \quad (8)$$

Figure 19:
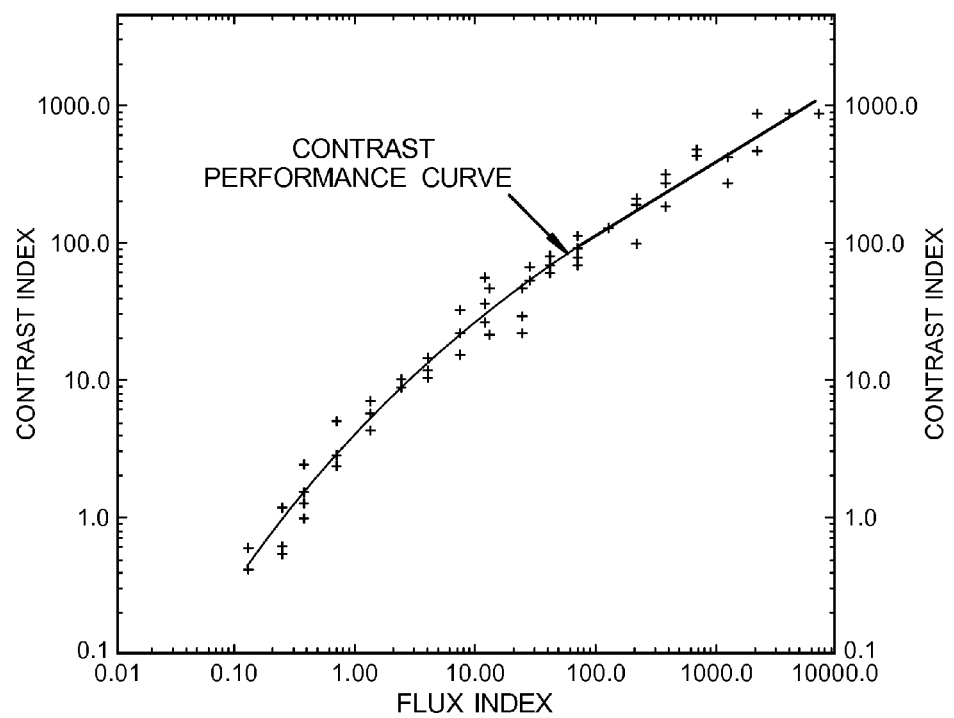
FIG. 19 shows mapping from selected smallest pins to ExLCD contrast measure plot.

The smallest (2.0 mm) pin is currently not carried onto the ExLCD contrast measurement plot because there is no way to be sure it is the smallest pin detectable. Therefore, for this example, as shown in FIG. 18, the first two contrast measurements, [47,69] are carried onto the ExLCD contrast measurement plot at the Flux Index location (10.0) indicated for Test 32 in Table 2. In FIG. 19, the collection of ordered pairs are shown along with a Contrast Performance Curve that is a least-squares fit to the collection of ordered pairs.

EXLCD Detectability

Figure 30:
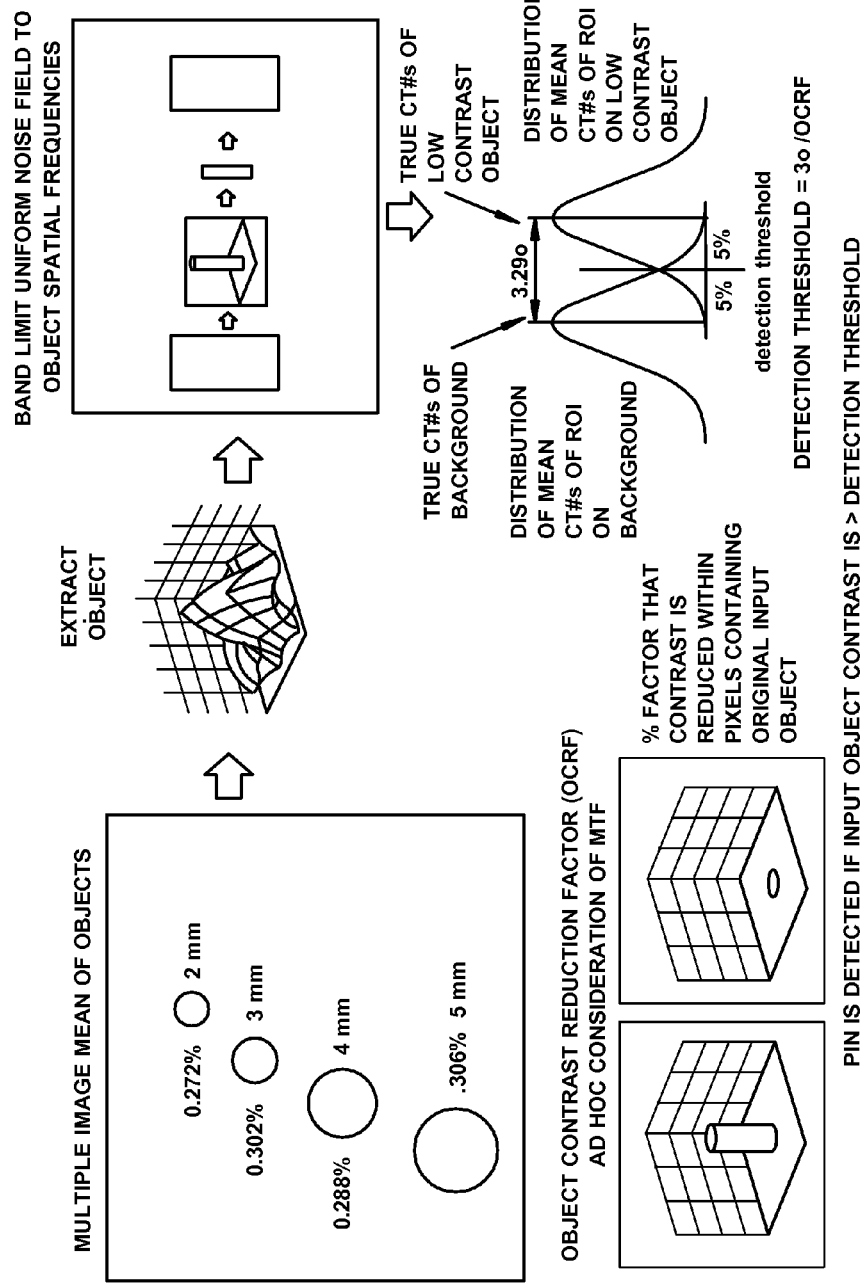
FIG. 30 is a preferred embodiment of an ExLCD detectability algorithm.

The ExLCD process can incorporate any combination of detectability methods listed above, as shown for example in FIG. 30. The efficacy of the various detectability methods using the ExLCD algorithm is compared in a later section.

As with the current single protocol LCD method, single or multiple observer methods may be used with the ExLCD process. This implies that each human observer will examine each of the 44 images and assess the smallest pin detectable for each of the three contrast sets. An observer can complete the 44 images on average in less than 30 minutes.

Results of multiple human observers analyzing various ExLCD experiments demonstrate that there is a wide variation in results among human observers. In fact, it is proven that the variation among observers is large compared to the expected measurement variations among CT scanners.

Figure 20:
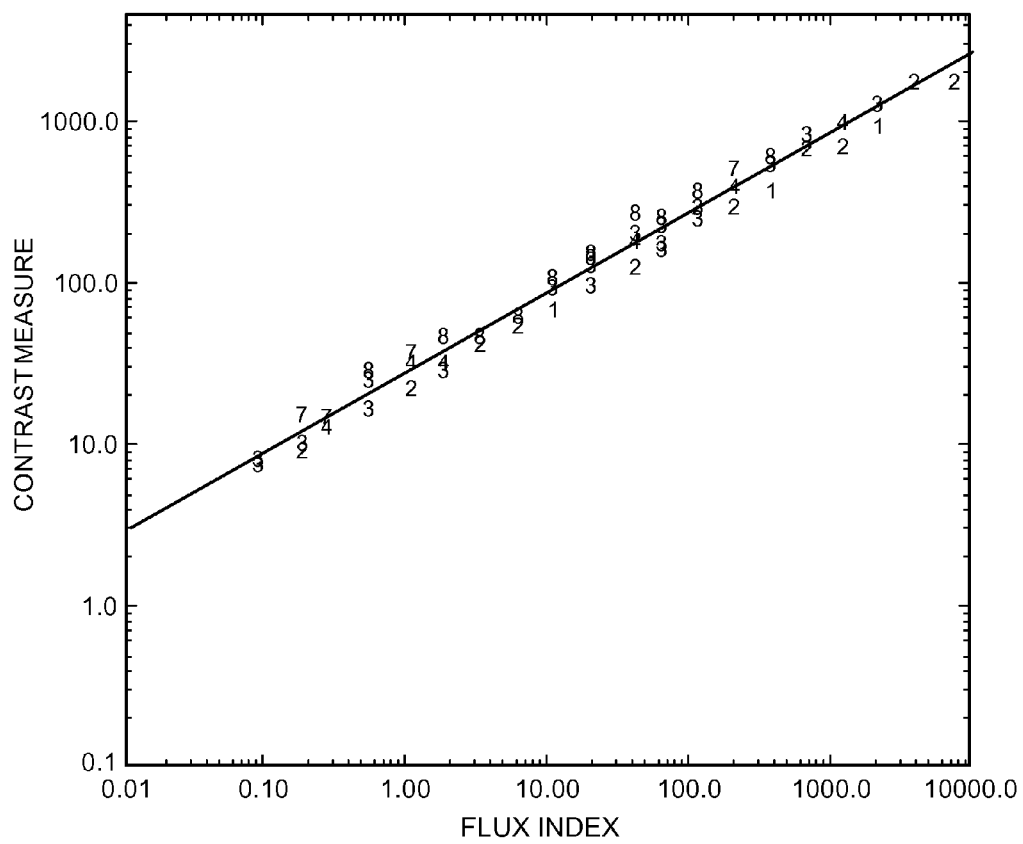
FIG. 20 shows ExLCD contrast measures derived from Statistical Method.

A statistical method from a single protocol LCD method is applied to the ExLCD process, for example as described in the book, *Computed Tomography: Principles, Design, Artifacts and Recent Advances*, by Jiang Hsieh, the entirety of which is hereby incorporated by reference, and which is variation of the Contrast Discrimination Factor (CDF) described in ASTM 1695-95. The algorithm as described therein is applied to each of the 44 images generated for the ExLCD process. The smallest pin in any contrast level that achieves the background separation will be selected for that contrast set. That is, if the ideal contrast value is at or above the noise standard deviation computed for that pin size, the contrast measure for that pin and that contrast level will be placed onto the ExLCD contrast measure graph as illustrated in FIG. 20.

The statistical method generates the most consistent contrast performance curves but suffers from two problems: (1) it tends to bias all results toward higher contrast measures and (2) it cannot generate accurate contrast measures when non-linear or iterative reconstruction is used.

The Rose criterion has long been a robust standard for image detectability analysis of low contrast objects embedded in a white noise background, for example by the Rose Criterion Derivation as well known in the art. It relates the (1) object size, (2) measured object contrast and (3) the background noise (pixel standard deviation) in a formula that establishes a detectability index, v, $$v = \frac{Cp}{\sigma}\frac{\sqrt{\pi}}{2S} \tag{9}$$

where C is the measured object contrast, p is the pin diameter, S is the image pixel size and σ is the measured standard deviation of the background noise. Note that in this formula, the measured contrast level is indicated with an upper case C, differentiating it from the nominal contrast level of Equation 1, indicated with a lower case c.

Figure 21:
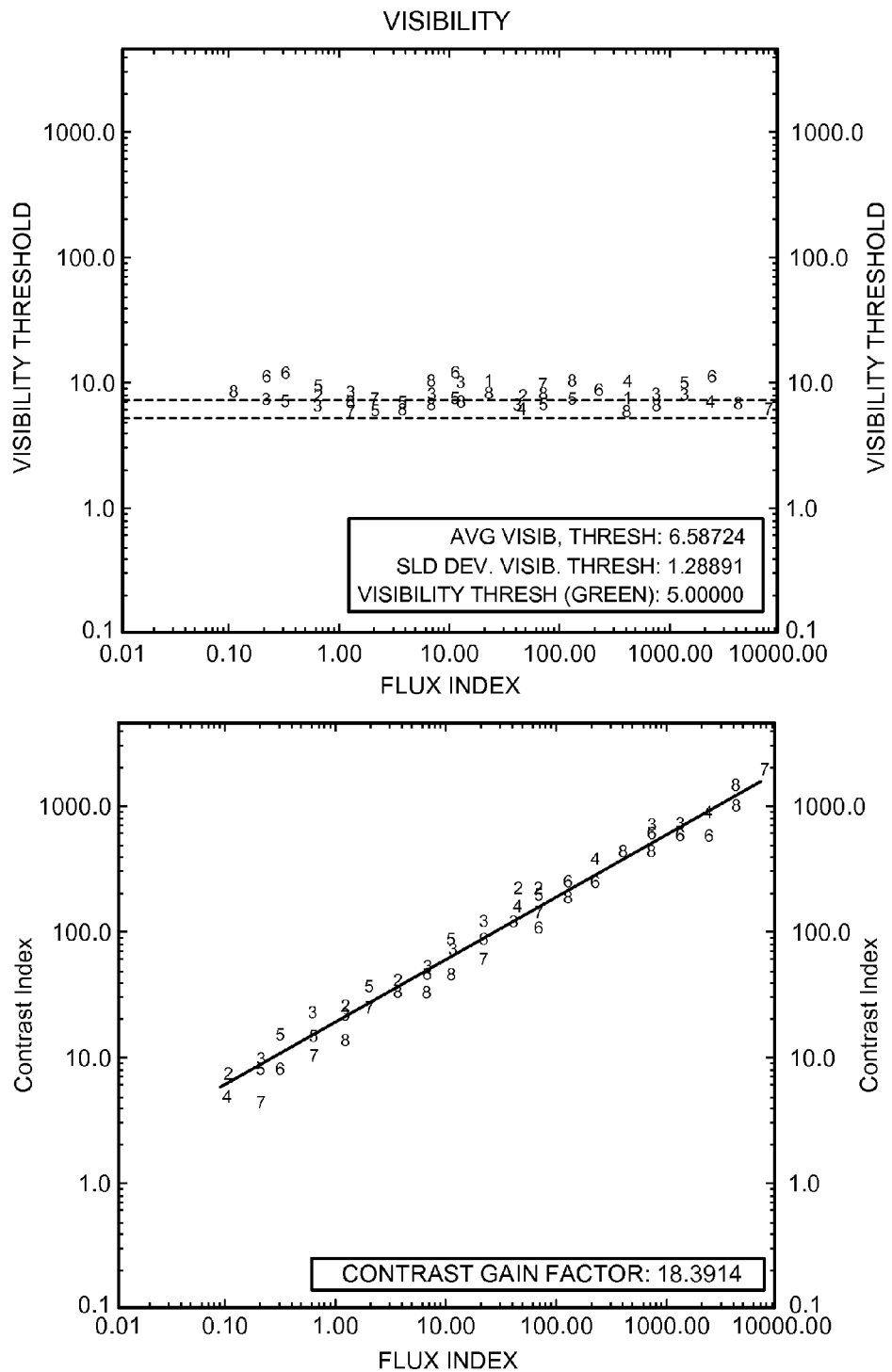
FIG. 21 is the Rose criterion detectability index (top) and corresponding ExLCD contrast measure (bottom)

Detectability values are computed for each of the contrast levels for each of the 44 image slices available. The detectability values that are at or above the detectability threshold are selected as "detectable." Although the Rose Criterion derivation suggests a threshold of 4, we determined that a threshold of 5 was more consistent with human observer results. The selected detectability values are shown in the upper plot in FIG. 21. For each detectable pin, an ExLCD Contrast Index value is computed according to Equation (1) and that value is plotted on the ExLCD contrast measure graph, FIG. 21, lower plot.

The Rose criterion definition clearly relies on measured contrast in calculating the detectability index. It is instructive, however, to investigate the behavior of the Rose detectability method if ideal or nominal contrast is used instead of the measured contrast. That is, a Rose-Ideal detectability index could be defined by the following formula.

$$v_I = \frac{cp}{\sigma}\frac{\sqrt{\pi}}{2S} \tag{10}$$

The Matched Filter detectability method draws on the formulation for the Ideal Bayesian Observer (IBO). The ideal observer is one whose data analysis performance is the highest possible. The Matched Filter detectability method utilizes the formulation of the IBO ideal decision maker, $$SNR^2 = K^2 \int \frac{|f(\tau)|^2 MTF^2(\tau)}{W_n(\tau)} d\tau \tag{11}$$

where f is the Fourier transform of the ideal object, K is the large area transfer factor, MTF is the system Modulation Transfer Function (MTF) and $W_n$ is the noise power spectrum.

In Equation 11, the term, $|f(\tau)|^2 MTF^2(\tau)$, is effectively the power spectrum of the reconstructed object with no noise. This formulation works for a linear, shift-invariant system but is not adequate if we wish to model non-linear reconstruction methods. In order to generalize Equation (11) for the non-linear case, we replace $|f(\tau)|^2 MTF^2(\tau)$ with $|\hat{f}_o(\tau)|^2$, the power spectrum of the object-dependent reconstruction of ideal object, o. Thus we have, $$SNR_o^2 = K^2 \int \frac{|\hat{f}_o(\tau)|^2}{W_n(\tau)} d\tau. \tag{12}$$

And the Matched Filter detectability index, $v_o$, can be written as $$v_o = SNR_o = K\sqrt{\int \frac{|\hat{f}_o(\tau)|^2}{W_n(\tau)} d\tau}. \tag{13}$$

The object, o, is "visible" if $v_o$ is greater than a predetermined threshold.

Figure 22:
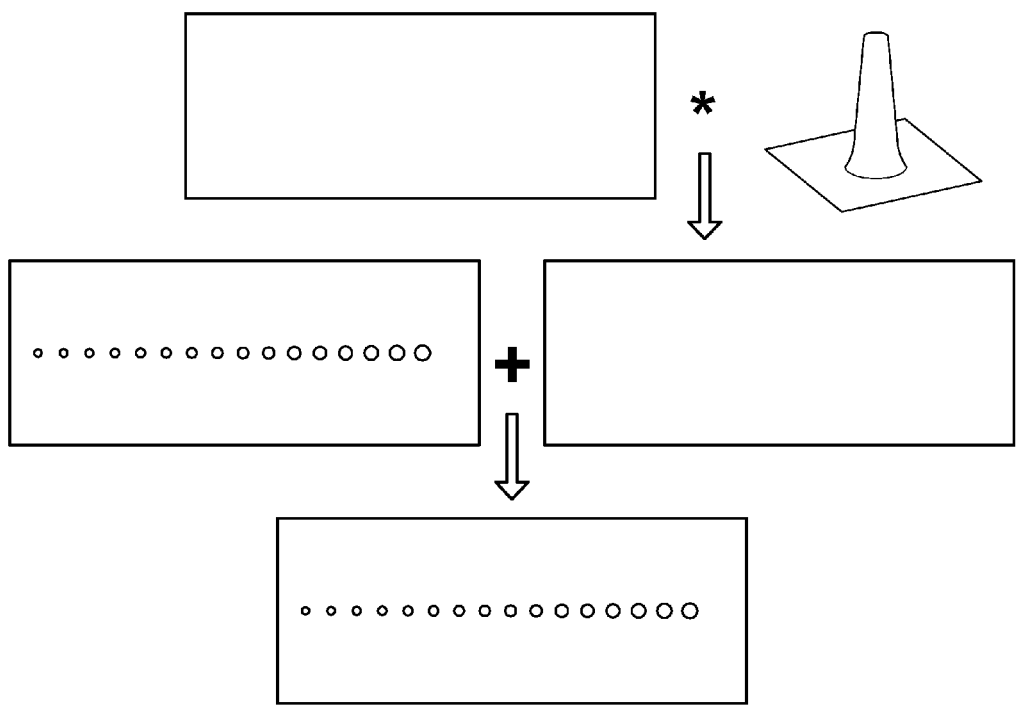
FIG. 22 an illustration of Matched Filter detectability analysis wherein the reconstructed image noise field (top row) is convolved with the ideal reconstructed image of the pin and a sequence of 15 ideal reconstructed pins is combined with the filtered noise field (middle row) to produce an image (bottom row) that illustrates the contrast amplitude necessary to achieve visibility above the specified threshold.

The Matched Filter method is illustrated intuitively with the images and graphics presented in FIG. 22.

Computing $v_o$ with real image data poses significant numerical challenges. The overall constant K is implicit in our ExLCD process and does not vary with the CT scanner. The noise power spectrum, $W_n$, can be computed as the radial average of the 2D Fourier transform of a large uniform noise region of pixels. It is critical that this region be highly uniform, free from even minor cupping, bands or rings. Of course, the result must be scaled appropriately for pixel size and number of pixels.

The object-dependent Fourier transform of the object, $|\hat{f}_o(\tau)|^2$ will be computed as the radial average of the 2D Fourier transform of the reconstructed object. It is critical that the small region of pixels containing the object be selected to reduce noise contamination. As with the noise power spectrum, the result must be scaled appropriately for pixel size and number of pixels.

EXLCD Performance Function

Figure 23:
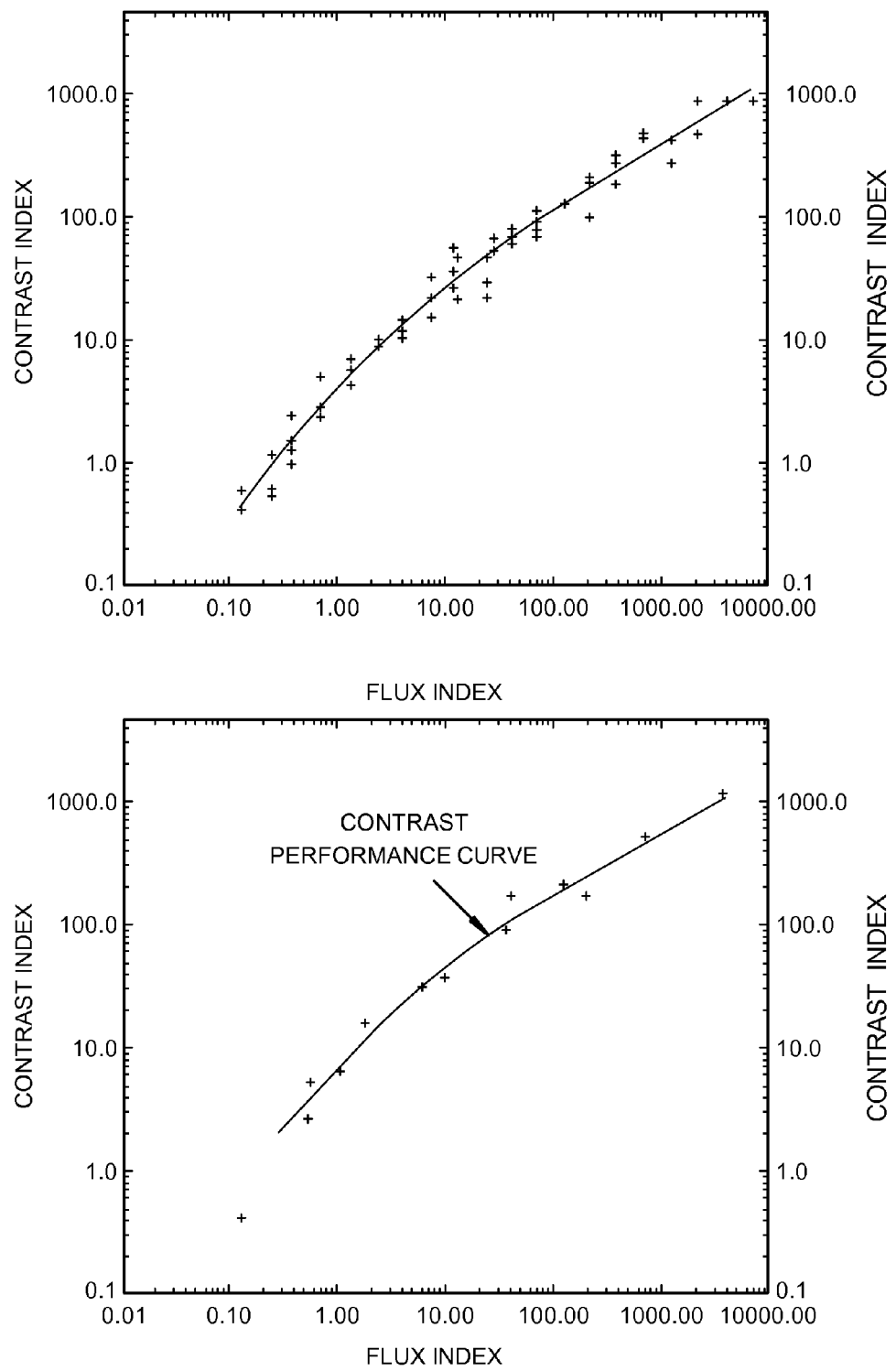
FIG. 23 is (top) a collection of ordered pairs, [relative flux, contrast measure] and (bottom) least-squares fit to 2-parameter equation.

As described above, the output of any of the detectability methods applied to the 44 image slices is a collection of ordered pairs, [Flux Index, Contrast Index], corresponding to the smallest pins that are "detectable" for any applicable contrast level. This collection of ordered pairs can be plotted on a log-log scale as shown in the upper plot of FIG. 23 and then used to build the ExLCD Performance Function. As one method, data points are then fit to a 2-parameter equation involving (1) quantum detection efficiency and (2) system/electronic noise. The lower plot in FIG. 23 illustrates a curve generated by a least-squares fit.

In the absence of non-linear reconstruction methods, it can be shown that the ExLCD Contrast Index is approximately proportional to signal-to-noise.

$$M \cong K \frac{\rho J}{\sqrt{\rho J + e^2}}, \quad (14)$$

where [J, M] represent the ordered pairs, [Flux Index, Contrast Index]. For each collection of ordered pairs, we can determine values for ρ and e that best fit the measured ordered pairs. In the analysis reported in the Results and Experiments section, ρ corresponds to the Contrast Gain Factor and e corresponds to the standard deviation of the system/electronic noise.

Figure 24:
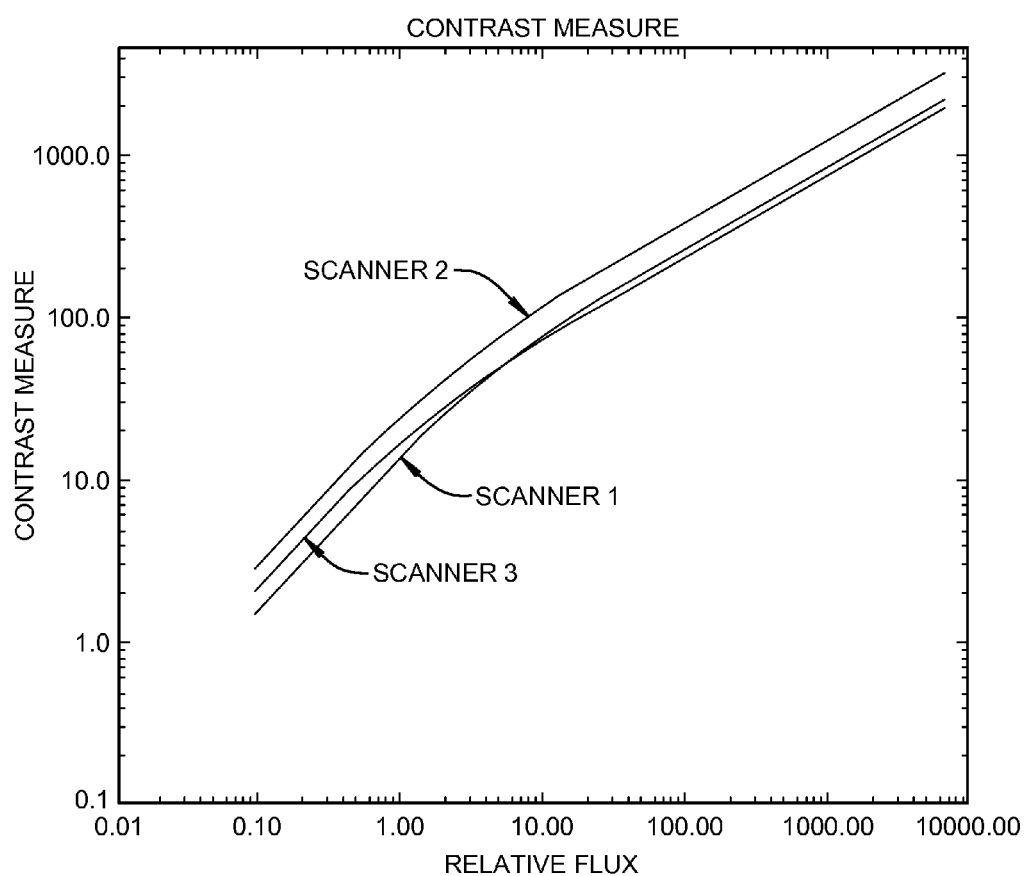
FIG. 24 is a comparison of contrast performance curves for three scanners.

The parameters, ρ and e, may provide definitive characterization of a CT scanner. In the Results and Experiments section, we illustrate how the different detectability methods react to specific scanner changes that will affect ρ and e. Clearly, a scanner has better performance when the ExLCD process reports higher values for contrast gain and lower values for electronic noise. For example, from the comparison plot of FIG. 24, it is shown that:

1. Scanner 2 has a higher (better) contrast gain than Scanner 1
2. Scanner 3 has a somewhat lower (worse) contrast gain than Scanner 2
3. Scanner 3 has lower (better) electronic noise than Scanner 1

Figure 10:
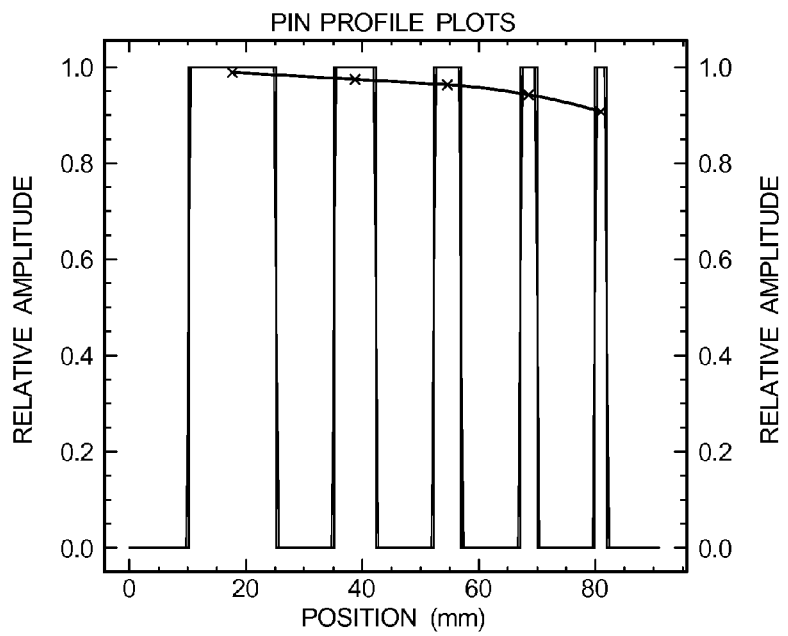
FIG. 10 is an illustration of contrast reduction due to pin blurring; (top) blurring in a head scan; and (bottom) blurring in a body scan protocol.
Figure 10:
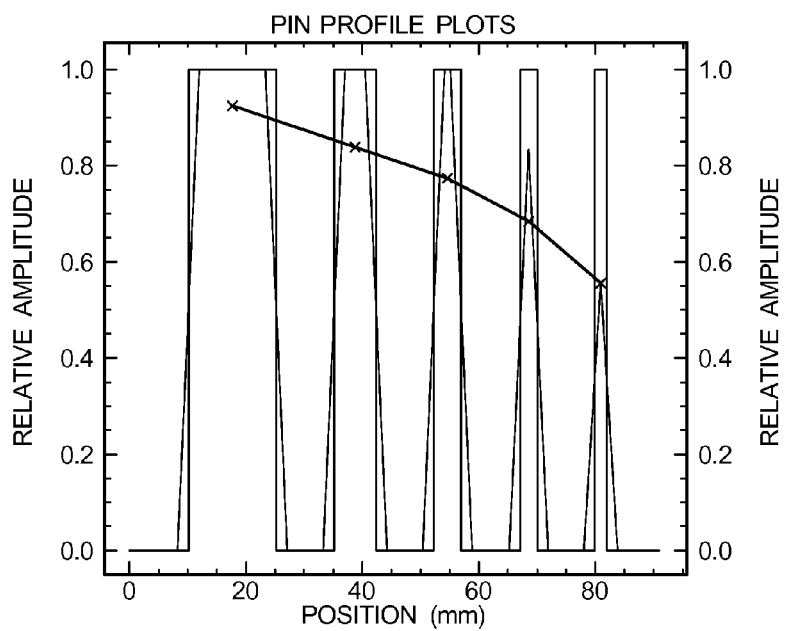
Figure 11:
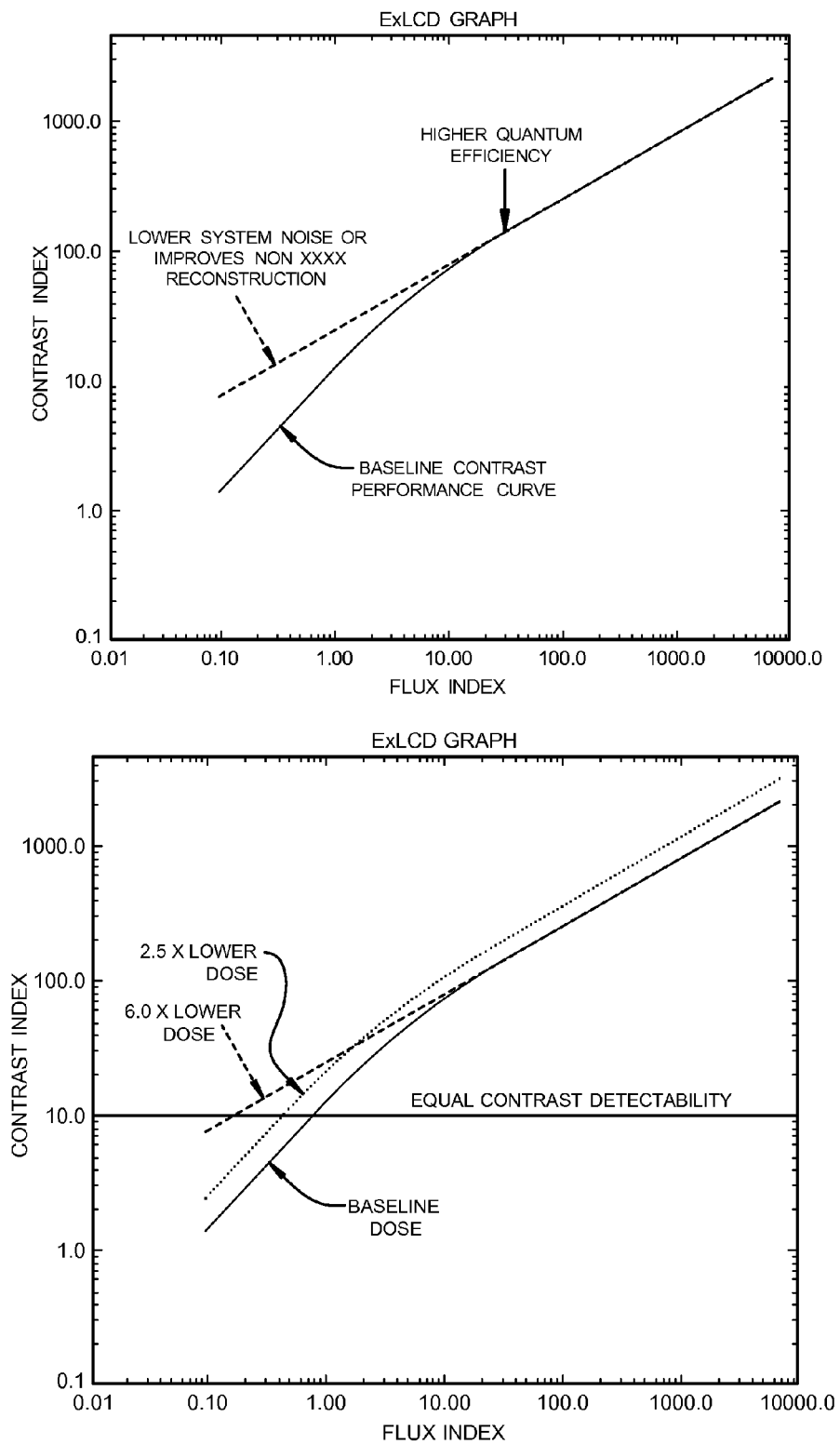
FIG. 11 (top) shows the impact of system characteristics on contrast performance cure and (bottom) shows the dose comparison for equivalent contrast detectability for three different contrast performance curves.
Figure 12:
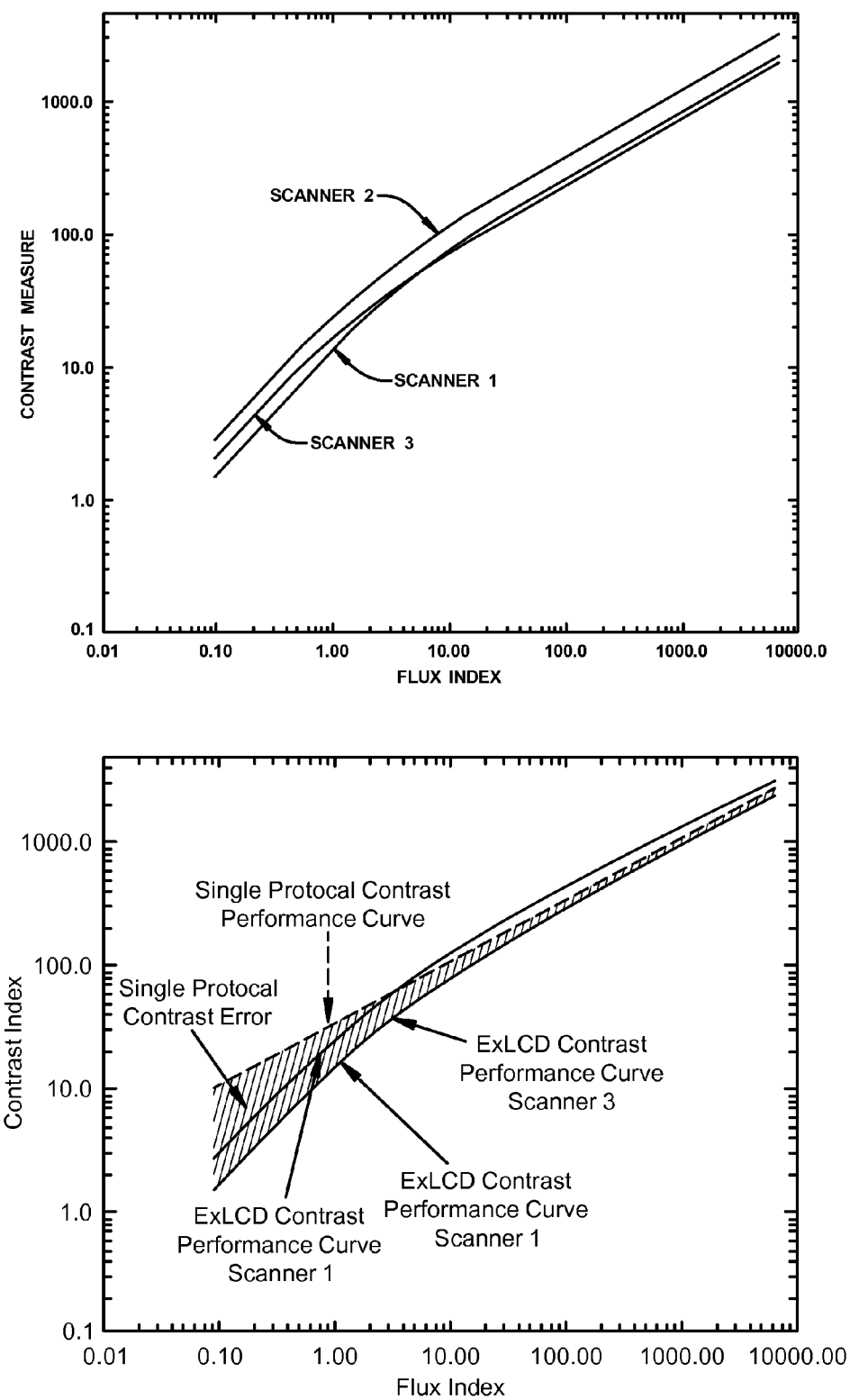
FIG. 12 (top) is a comparison of contrast performance curves for three representative CT scanners and (bottom) are contrast performance curves for three representative CT scanners overlaid on error in single protocol contrast.
Figure 25:
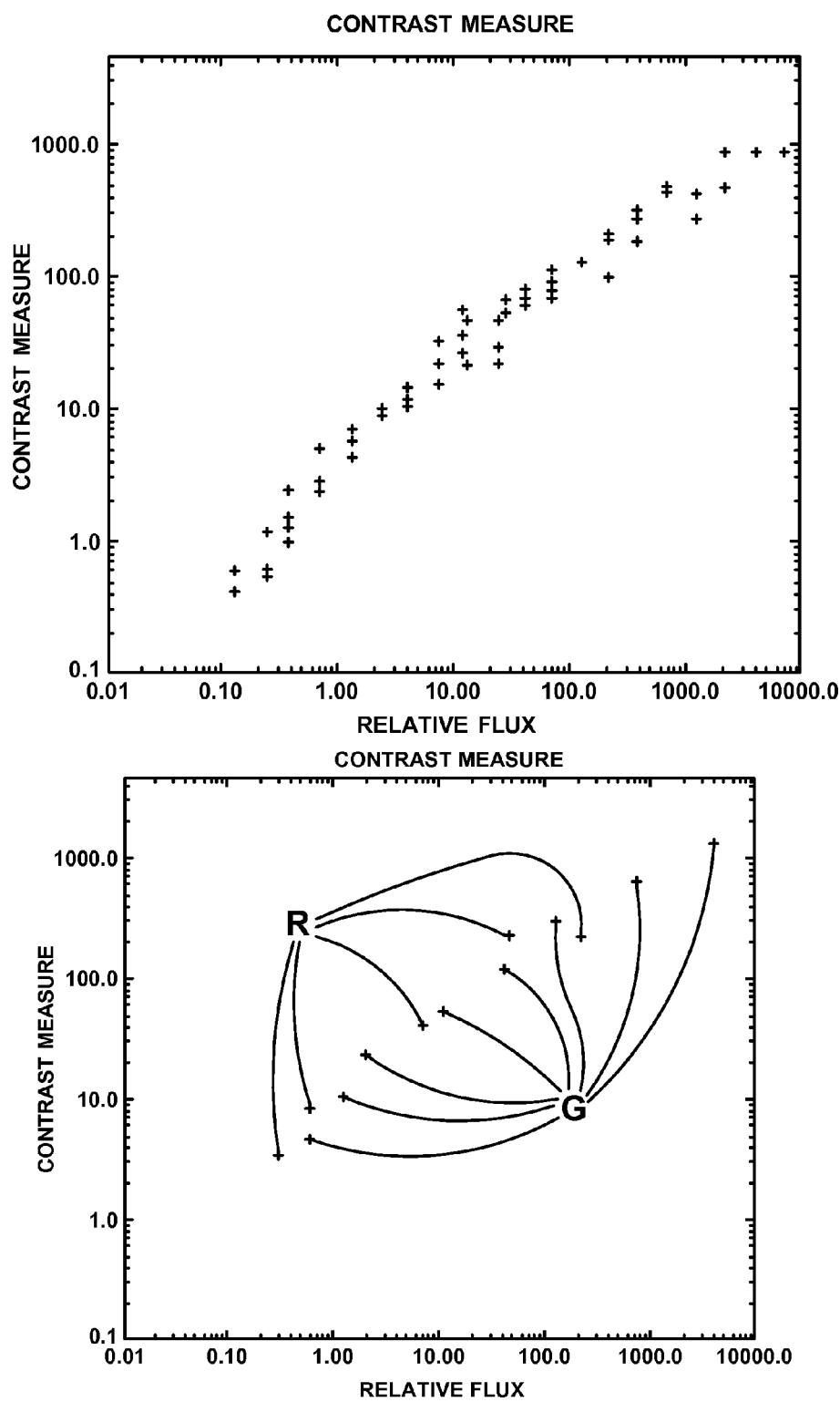
FIG. 25 is (top) a large pin contrast performance cure wherein pins >2.5 mm and (bottom) a small pin contrast performance curve (red=2.5 mm, green=2 mm)
Figure 26:
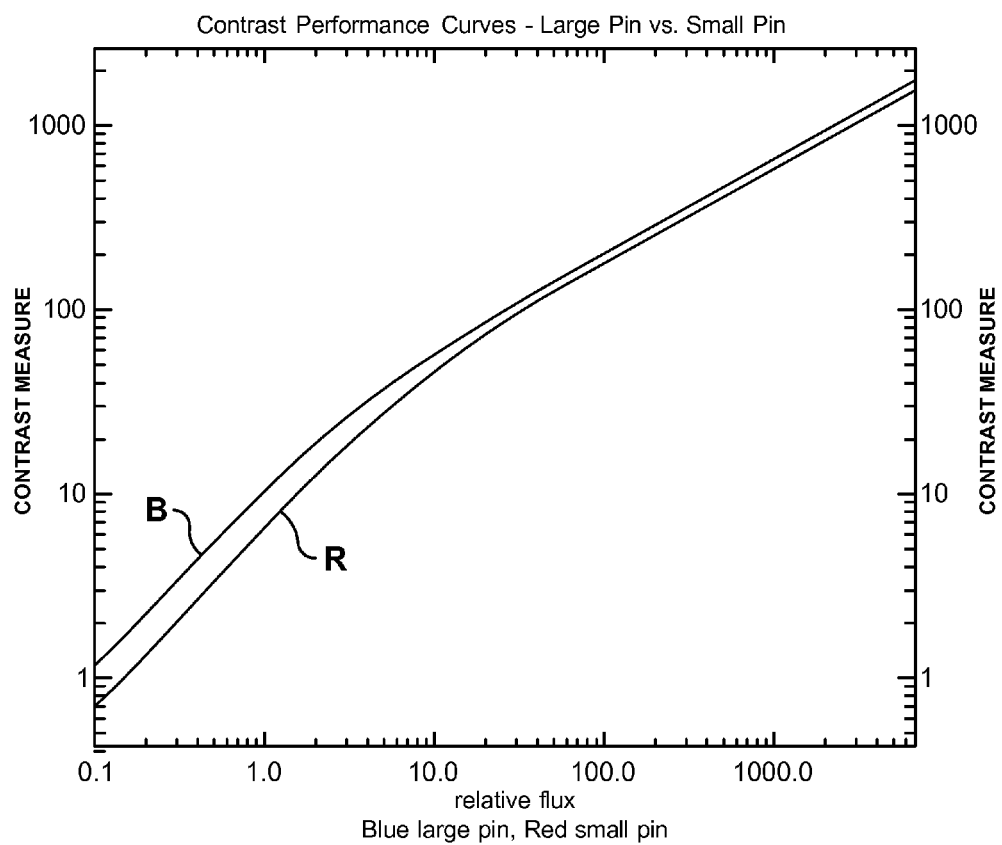
FIG. 26 is a comparison of contrast performance for large pin (blue) and small pin (red)
Figure 27:
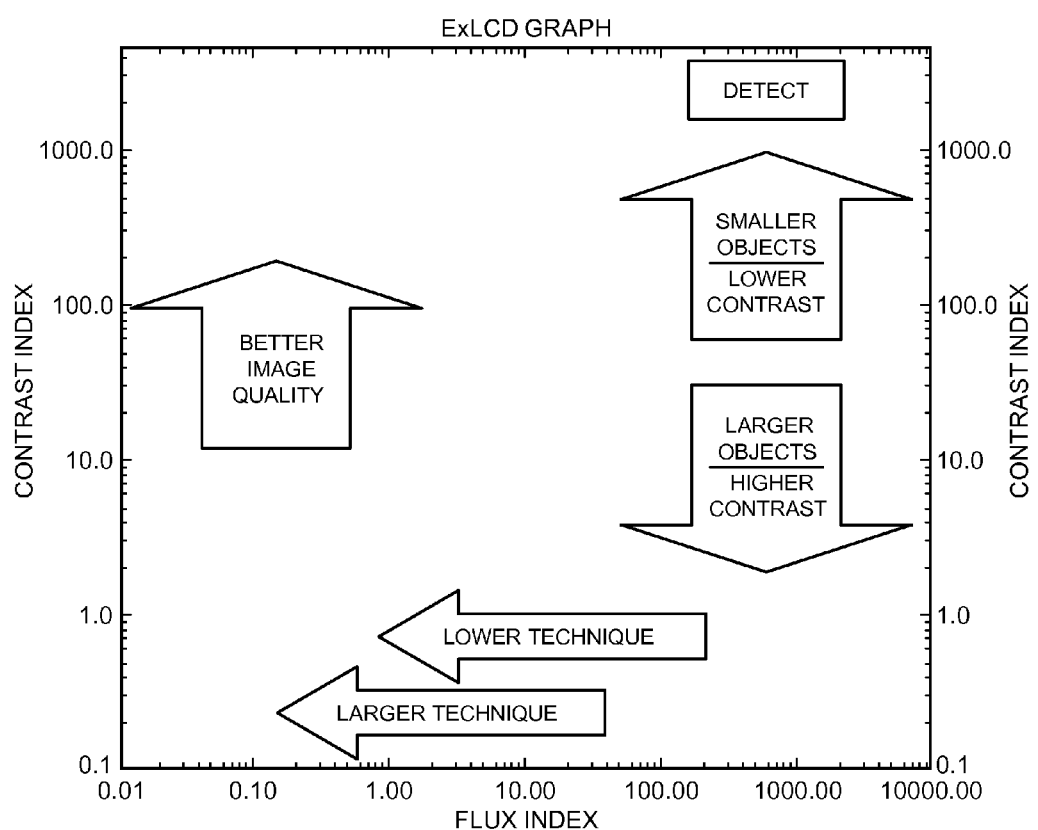
FIG. 27 is an ExLCD graph wherein contrast index tracks detectability/image quality and flux index tracks does/patient size.

As illustrated in FIG. 10, when a smaller pin is blurred by the system MTF, there may be a corresponding reduction of contrast. That is, a highly filtered noise spectrum with a highly filtered object will result in a lower detectability score than a reconstruction process (e.g. non-linear reconstruction) that results in a highly filtered noise spectrum but is capable of retaining the spatial geometry of the original object. This phenomenon will typically only be observable and measurable for the smaller contrast pins. Therefore, the ExLCD method includes a small pin performance curve, estimated from the contrast measurements involving the pins that are impacted by the MTF. In FIG. 25 contrast measures are shown for large pins (upper) and small pins (lower). A comparison is shown in FIG. 26.

Phantom Calibration

Each physical ExLCD phantom will undoubtedly have some variation from the phantom design. The ExLCD process, therefore, will incorporate a calibration component that will determine and record actual contrast values and actual pin location values. The actual contrast values, determined by the calibration, will then be used as the nominal contrast values (lower case c) for all ExLCD measurements. Actual pin location values will be used to improve the accuracy of measured contrast values (upper case C) for any non-observer detectability determination.

The calibration component will effectively compensate for x-ray spectral variations between scanners. Also, the calibration component will include a phantom manufacturing tolerance check. If the phantom slices are out of tolerance in contrast, pin size or pin locations, it will be reported.

Results and Experiments

In order to assess the value of the ExLCD process, we simulated a variety of scanner configurations. We used a full-featured fan-beam CT scan simulator to generate CT measurement data. The fan-beam simulator includes the capability to simulate both quantum and electronic noise. For these experiments, only quantum and electronic noise were varied. The remaining configuration parameters, listed in Table 5 were kept constant.

TABLE 5

Scan and reconstruction parameters for simulation experiments

| Parameter | Value |
|---|---|
| Source to detector distance (cm) | 115 |
| Source radius (cm) | 62.5 |
| Detector pitch (cm) | 0.1 |
| Detector height (cm) | 0.1 |
| X-ray spectrum | Mono-energetic |
| Scan diameter for 40 cm phantom | 50.0 |
| Scan diameter for 20 cm phantom | 25.0 |
| View spacing (deg) | 0.45 |
| Reconstruction image size | 512 × 512 |
| Reconstruction image radius (cm) | 11.0 |

In Table 6, all of the configurations are listed and results are recorded for both contrast gain and electronic noise for the human observers, Rose, Rose-Ideal and the statistical method. The contrast gain is expected to change as the square root of the quantum efficiency whereas we expect the electronic noise to change directly with the simulated electronic noise.

TABLE 6

Contrast gain and electronic noise fits for various experiments for human observers, Rose, Rose-Ideal and the statistical method

| Run # | Quantum Efficiency | Electronic Noise | Contrast Gain | | | | | | | | Electronic Noise | | | | | | | | Fit Parms |
|---|---|---|---|---|---|---|---|---|---|---|---|---|---|---|---|---|---|---|---|
| | | | Observers | | | | | Rose | Rose Ideal | Stat | Observers | | | | | Rose | Rose Ideal | Stat | |
| | | | 1 | 2 | 3 | 4 | Ave | | | | 1 | 2 | 3 | 4 | Ave | | | | |
| 1 | Baseline | None | 15.6 | 13.9 | 21.4 | 20.6 | 17.9 | 18.4 | 23.8 | 28.2 | | | | | | | | | 1 |
| 2 | Half | None | | | | | | 13.3 | 16.3 | 20.0 | | | | | | | | | 1 |
| 3 | Double | None | | | | | | 26.7 | 33.4 | 39.6 | | | | | | | | | 1 |
| 4 | Baseline | Baseline | 20.2 | 19.6 | 31.9 | 21.4 | 23.3 | 20.2 | 26.1 | 28.7 | 34.8 | 36.8 | 61.8 | 29.7 | 40.8 | 35.3 | 61.0 | 50.9 | 2 |
| 5 | Half | Baseline | | | | | | 14.1 | 18.4 | 21.4 | | | | | | 30.8 | 54.0 | 54.7 | 2 |
| 6 | Double | Baseline | | | | | | 26.5 | 36.1 | 40.5 | | | | | | 24.3 | 53.6 | 54.3 | 2 |
| 7 | Baseline | Half | | | | | | 20.8 | 25.5 | 27.6 | | | | | | 20.1 | 28.3 | 25.3 | 2 |
| 8 | Baseline | None | 15.7 | 13.8 | 21.3 | 20.1 | 17.7 | 18.2 | 24.3 | 27.9 | 5.3 | 3.1 | 7.0 | 2.2 | 4.4 | 4.1 | 6.4 | 4.1 | 2 |
| 9 | Half | None | | | | | | 12.9 | 16.8 | 20.0 | | | | | | 2.2 | 5.6 | 4.0 | 2 |
| 10 | Double | None | | | | | | 26.1 | 34.1 | 38.9 | | | | | | 4.0 | 8.4 | 4.1 | 2 |

Not Processed        Not Applicable

The measurement error is computed for the fits from line numbers 8-10 in Table 6. The standard deviation of those errors in contrast gain units is given in Table 7.

TABLE 7

Measurement error for fits from line numbers 8-10 from Table 6.

| Quantum Efficiency | Electronic Noise | Observers | | | | Rose | Rose Ideal | Stat |
|---|---|---|---|---|---|---|---|---|
| | | 1 | 2 | 3 | 4 | | | |
| Baseline | None | 3.18 | 2.74 | 3.29 | 2.67 | 2.79 | 1.59 | 2.25 |
| Half | None | | | | | 3.28 | 1.54 | 2.28 |
| Double | None | | | | | 2.43 | 1.58 | 2.36 |

From the foregoing, it is disclosed and apparent that:
1. The ExLCD process can successfully characterize the contrast performance of a CT scanner over the entire flux range. It is also adaptable to other radiography applications such as digital radiography, mammography, nuclear medicine and SPECT.
2. A single LCD measurement provides no information about the contrast performance of a scanner in the lower flux regions including (1) body scans at lower dose, (2) scans for a large body, (3) fast scans.
3. With the ExLCD process, human observer detectability determination is much less consistent than either of the automatic methods: statistical and Rose. In fact, observer detectability determination is not accurate enough to differentiate the contrast performance among typical commercial scanners.
4. With the ExLCD process, the Rose method is much closer to the human observer results than the statistical method.
5. Both the Rose method and the statistical method accurately track expected changes in contrast gain with and without the presence of electronic noise.
6. For the Rose method, the electronic noise parameter is not consistent with changes in quantum efficiency. For the statistical method, the electronic noise parameter is consistent within 8% with changes in quantum efficiency.
7. For the statistical method, the electronic noise parameter accurately tracks expected changes in electronic noise.
8. Based on visual analysis of the ExLCD contrast measures, the Rose method is very noisy compared to the Rose-Ideal and the statistical methods. This is because the Rose method uses a contrast value for each pin, measured in the image at the known location of the pin. This indicates that it will be necessary to average contrast values across multiple slices.

The system and method of the disclosure also provide the following functions, features and advantages:

A performance function for a radiographic imaging system (such as CT) that characterizes detectability over the operating range of the system.

A performance function that can be associated with clinical performance related to dose utilization.

The ExLCD performance function is automatically calculated.

The calculation method is responsive to non-linear and iterative image reconstruction methods.

A special phantom or set of phantoms can be used with a large array of objects of various sizes and contrasts designed to cover the range of lowest to highest possible flux conditions.

Figure 28:
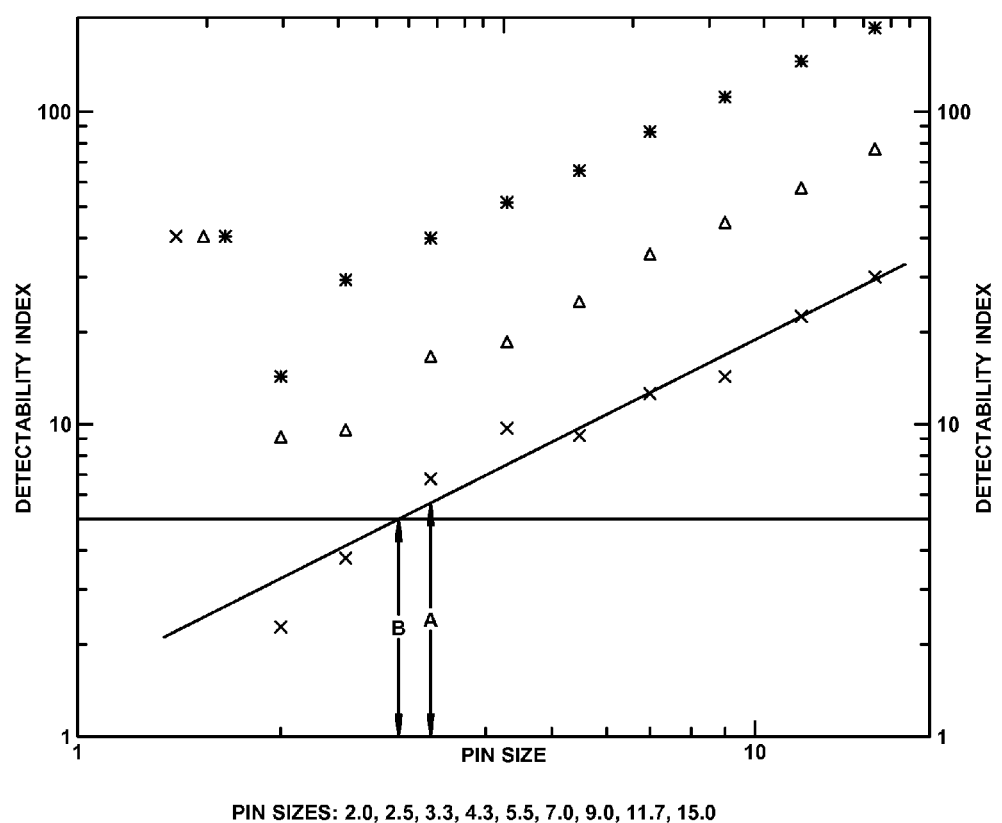
FIG. 28 is a graph wherein green "X" pints indicate detectability values for each object size for a given contrast level; thick gray line shows a linear fit of detectability values; location "A" indicates the smallest object size based on the smallest distinct object above the threshold; location "B" indicates the smallest object size based on a fit using all object sizes.

The ExLCD method can be enhanced as shown in FIG. 28 by using all object sizes for a given contrast level to determine the smallest detectable object. This concept can result in the improvement of accuracy of detection of the "smallest pin size" by fitting the points to a line and determining where the fitted line crosses the detectability threshold. Similarly, a fit could be made using all object contrasts for given object size.

The ExLCD method requires that the phantom be calibrated to account for manufacturing variances.

The ExLCD phantom calibration methodology includes scanning the phantom and reconstructing images using a linear reconstruction method. Each test object in the phantom images is then deconvolved with the MTF of the system to obtain a representation of the input object using the plurality of images to assure high signal-to-noise ratio for the objects.

The calibrated phantom may be scanned multiple times to assure good SNR performance with a set of protocols at strategic points in the scanner operating range.

A detectability calculation analyzes each object and noise spectrum for sets of objects within the band of contrast levels encompassing the threshold of detectability.

The detectability calculation may use a Non Pre-whitening Matched Filter Signal to Noise ratio where the object signal is reduced by the object contrast reduction factor.

The performance function can be used to duplicate clinical performance for any patient on a scanner that has been characterized.

The performance function provides an objective quantifiable scoring scale for qualitative clinical imaging.

The minimum clinical image quality scores can be determined and assigned for various clinical problems by medical researchers. For a particular patient and clinical problem, these scores can be used to determine the precise conditions of operation for a scanner that has been characterized that are required.

What is claimed is:

1. A device comprising:
   a least one data processor associated with at least one computed tomography image acquisition system;
   an input operable to receive base relationship data representative of a mathematical relationship derived from a plurality of flux levels of a plurality of radiographic phantom images;
   the at least one data processor operable to associate image quality metrics correspondingly with flux levels in accordance with the base relationship data;
   a memory operable to store the base relationship data;
   an output operable to output display data for display of a plurality of radiographic anatomical images;
   an input operable to receive image quality selection data corresponding to at least one selected image quality metric selected by an associated user in accordance with the display of radiographic anatomical images;
   at least one data processor further operable to calculate a unique dose control signal for each of a plurality of radiographic imaging operations in accordance with application of the image quality selection data to corresponding, preassociated relationship data; and
   an output operable to relay each dose control signal to an associated one of the plurality of radiographic imagers.

2. The device of claim 1 further comprising a CT scanner comprising at least one of the radiographic imagers.

3. The device of claim 2 wherein the CT scanner is operable in a plurality of imaging modes.

4. The device of claim 1 wherein the relationship data is comprised of a data relationship table.

5. The device of claim 1 wherein the computer is further operable to generate the relationship data in accordance with a preselected relationship curve.

6. The device of claim 5 wherein the relationship curve is associated with a predefined function.

7. The device of claim 1 wherein the image quality metric is associated with detectability of at least one physiological state.

8. The device of claim 1 wherein the image quality metric is associated with at least one image artifact.

9. The device of claim 1 wherein the image quality selection data is comprised of a relationship between image quality and patient size.

10. The device of claim 9 wherein patient size is comprised of a water equivalent diameter.

11. A method comprising:
   storing, in an associated memory, relationship data corresponding to a relationship between image quality and flux levels associated with a plurality of radiographic phantom images obtained from a plurality of radiographic imaging operations at varying radiation levels;
   outputting display data corresponding to a plurality of radiographic anatomical images;
   receiving image quality selection data corresponding to a selected image quality metric from an associated user in accordance with display data;
   receiving device data corresponding to each of the plurality of radiographic imagers;
   calculating, in an associated computer, a unique dose control signal for each of a plurality of radiographic imaging operations in accordance with application of the image quality selection data and device data for each of the radiographic imaging devices to the relationship data; and
   outputting each dose control signal to an associated one of the plurality of radiographic imagers.

12. The method of claim 11 further comprising receiving the device data from a plurality of radiographic imagers disposed in a CT scanner.

13. The method of claim 11 further comprising operating the CT scanner in plurality of imaging modes.

14. The method of claim 11 further comprising retrieving the relationship data from a data relationship table in the memory prior to calculating.

15. The method of claim 11 further comprising retrieving the relationship data from the memory in accordance with a preselected relationship curve.

16. The method of claim 15 comprising retrieving the relationship data from stored in the memory in accordance with the preselected relationship curve associated with a predefined function.

17. The method of claim 11 wherein the image quality metric is associated with detectability of at least one physiological state.

18. The method of claim 11 wherein the image quality metric is associated with at least one image artifact.

19. The method of claim 11 wherein the image quality selection data is comprised of a relationship between image quality and patient size.

20. The method of claim 19 wherein patient size is comprised of a water equivalent diameter.

* * * * *